(12) United States Patent
Shelton, IV et al.

(10) Patent No.: US 8,419,749 B2
(45) Date of Patent: Apr. 16, 2013

(54) TISSUE RETRIEVAL DEVICE WITH REINFORCED POUCH AND VARIABLE VOLUME

(75) Inventors: Frederick E. Shelton, IV, Hillsboro, OH (US); Shailendra K. Parihar, Mason, OH (US); Michael S. Cropper, Edgewood, KY (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 406 days.

(21) Appl. No.: 12/693,498

(22) Filed: Jan. 26, 2010

(65) Prior Publication Data

US 2011/0184436 A1 Jul. 28, 2011

(51) Int. Cl.
*A61B 17/22* (2006.01)
(52) U.S. Cl.
USPC .......................................................... 606/127
(58) Field of Classification Search .................. 606/110, 606/113, 114, 115, 127, 128; 600/184
See application file for complete search history.

(56) References Cited

U.S. PATENT DOCUMENTS

| | | | |
|---|---|---|---|
| 5,190,555 A | 3/1993 | Wetter et al. | |
| 5,215,521 A | 6/1993 | Cochran et al. | |
| 5,320,627 A | 6/1994 | Sorensen et al. | |
| 5,337,754 A | 8/1994 | Heaven et al. | |
| 5,370,647 A | 12/1994 | Graber et al. | |
| 5,465,731 A | 11/1995 | Bell et al. | |
| 5,480,404 A | 1/1996 | Kammerer et al. | |
| 5,524,633 A | 6/1996 | Heaven et al. | |
| 5,647,372 A | 7/1997 | Tovey et al. | |
| 5,649,902 A | 7/1997 | Yoon | |
| 5,681,324 A * | 10/1997 | Kammerer et al. | ........... 606/113 |
| 5,735,289 A | 4/1998 | Pfeffer et al. | |
| 5,769,794 A | 6/1998 | Conlan et al. | |

(Continued)

FOREIGN PATENT DOCUMENTS

| | | |
|---|---|---|
| DE | 92 18 154 | 9/1993 |
| DE | 10 2008 019497 | 10/2009 |

(Continued)

OTHER PUBLICATIONS

International Search Report dated Apr. 4, 2011 for Application No. PCT/US2011/021817.

(Continued)

*Primary Examiner* — Ryan Severson
*Assistant Examiner* — Jonathan W Miles
(74) *Attorney, Agent, or Firm* — Frost Brown Todd LLC

(57) ABSTRACT

A tissue retrieval device includes a tubular member, one or more frame members, and a tissue retrieval bag. The tubular member is insertable into a patient through a trocar to open the bag within the patient to receive a tissue specimen. The internal capacity provided by the bag may vary based on the longitudinal position of the frame members. The bag may be stretchable to increase its internal capacity. At least one sidewall of the bag may include one or more reinforcement members, which may influence the way in which the bag stretches by restricting stretching of the bag in one or more directions while freely permitting stretching of the bag in one or more other directions. Part of the undeployed bag may be contained in a recess formed in the side of the tubular member, with a removable cap being positionable over the undeployed bag and recess.

14 Claims, 18 Drawing Sheets

U.S. PATENT DOCUMENTS

| | | | |
|---|---|---|---|
| 5,779,716 | A | 7/1998 | Cano et al. |
| 5,836,953 | A | 11/1998 | Yoon |
| 5,971,995 | A | 10/1999 | Rousseau |
| 6,409,733 | B1 | 6/2002 | Conlon et al. |
| 6,673,080 | B2 | 1/2004 | Reynolds et al. |
| 7,691,111 | B2 | 4/2010 | Bates et al. |
| 7,762,959 | B2 | 7/2010 | Bilsbury |
| 8,016,771 | B2 | 9/2011 | Orban, III |
| 2004/0138587 | A1 | 7/2004 | Lyons, IV |
| 2005/0267492 | A1* | 12/2005 | Poncet et al. ............... 606/114 |
| 2006/0200170 | A1 | 9/2006 | Aranyi |
| 2006/0247663 | A1 | 11/2006 | Schwartz et al. |
| 2007/0088370 | A1 | 4/2007 | Kahle et al. |
| 2011/0184311 | A1 | 7/2011 | Parihar et al. |
| 2011/0184430 | A1 | 7/2011 | Parihar et al. |
| 2011/0184431 | A1 | 7/2011 | Parihar et al. |
| 2011/0184432 | A1 | 7/2011 | Parihar et al. |
| 2011/0184433 | A1 | 7/2011 | Parihar et al. |
| 2011/0184434 | A1 | 7/2011 | Parihar et al. |
| 2011/0184435 | A1 | 7/2011 | Parihar et al. |

FOREIGN PATENT DOCUMENTS

| | | |
|---|---|---|
| EP | 0 578 997 | 1/1994 |
| EP | 0 950 376 | 10/1999 |
| WO | WO 93/15671 | 8/1993 |
| WO | WO 95/09666 | 4/1995 |
| WO | WO 98/38920 | 9/1998 |
| WO | WO 01/10308 | 2/2001 |
| WO | WO 2005/112783 | 12/2005 |

OTHER PUBLICATIONS

International Search Report dated Apr. 19, 2011 for Application No. PCT/US2011/021046.

International Search Report and Written Opinion dated Aug. 1, 2011 for Application No. PCT/US2011/021042.

International Search Report dated Oct. 11, 2011 for Application No. PCT/US2011/021049.

* cited by examiner

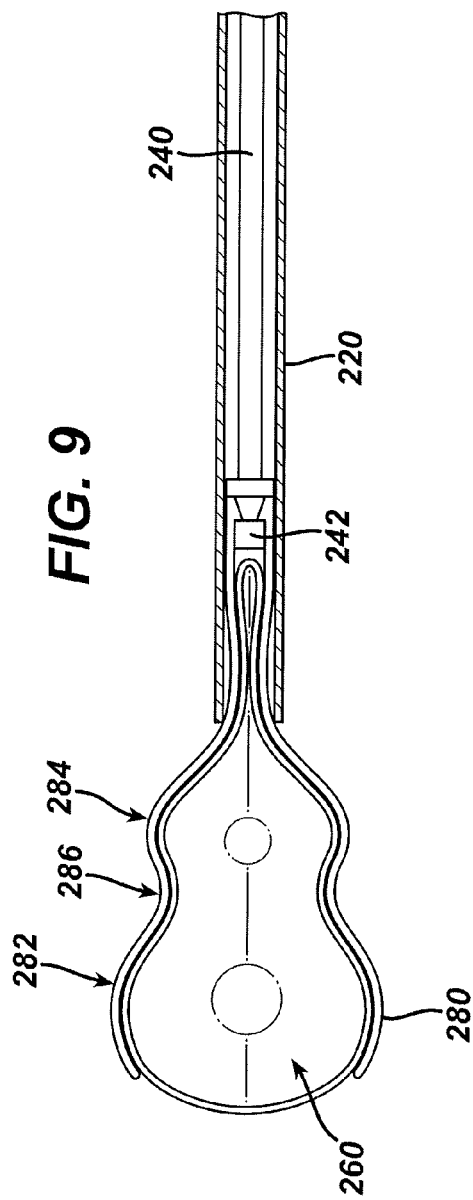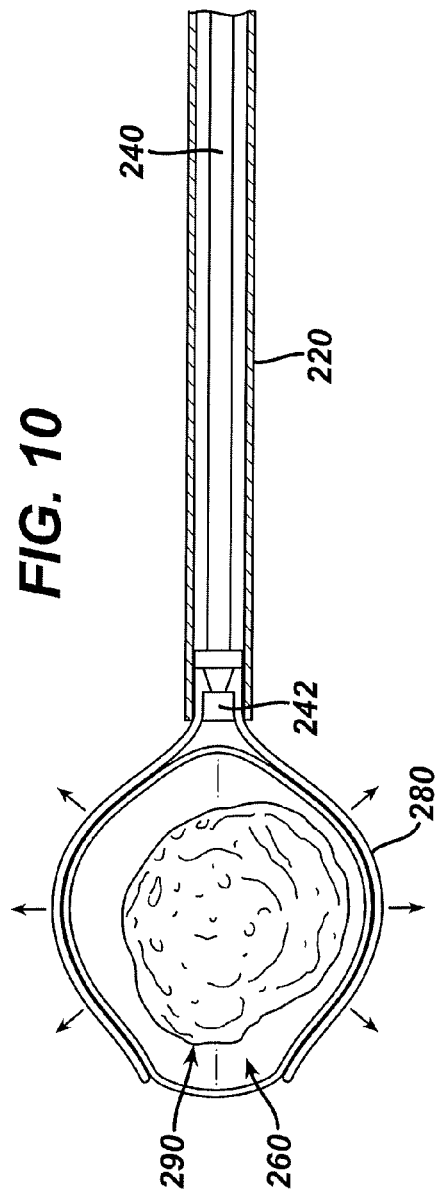

TISSUE RETRIEVAL DEVICE WITH REINFORCED POUCH AND VARIABLE VOLUME

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal cavity. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 9 is a top view of the distal end of the tissue retrieval device of FIG. 7, with the retrieval bag in a second deployed position, and with the introducer tube shown in cross section.

FIG. 10 is a top view of the distal end of the tissue retrieval device of FIG. 7, with the retrieval bag in the second deployed position, with the introducer tube shown in cross section, and with a tissue specimen within the retrieval bag.

Figure 1:
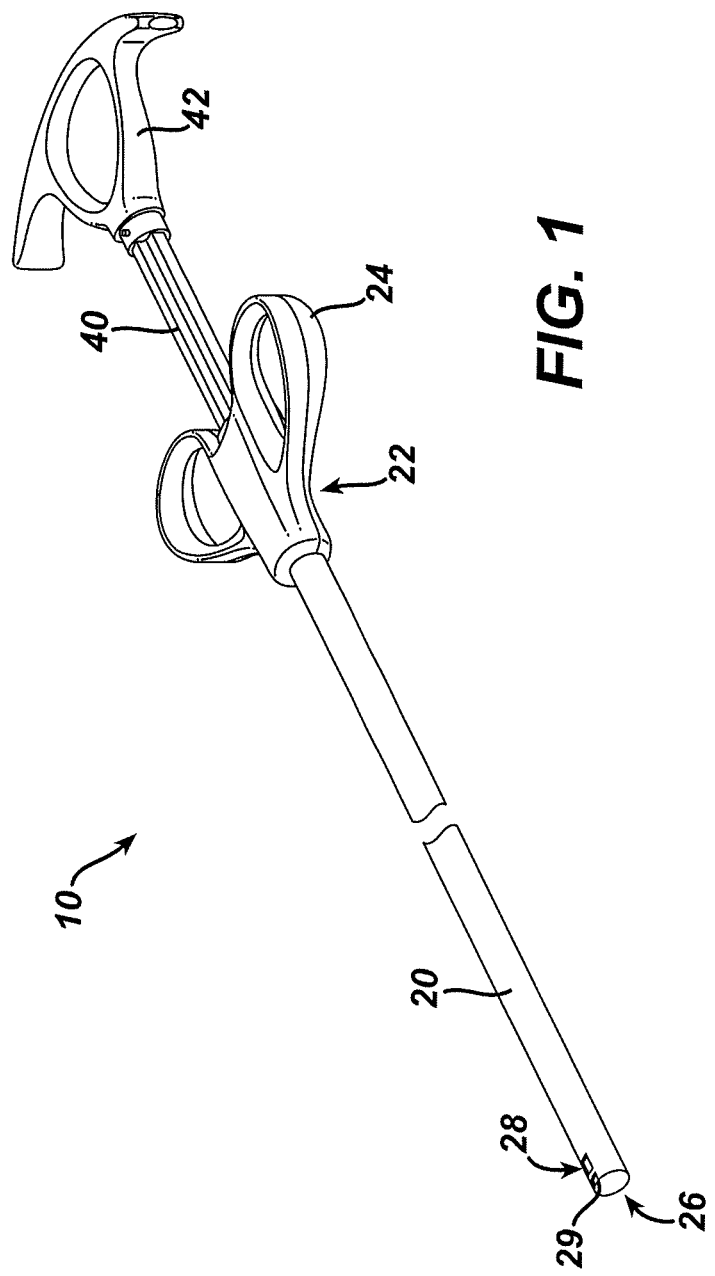
FIG. 1 is a perspective view of an exemplary tissue retrieval device, with a retrieval bag in a retracted position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Exemplary Tissue Retrieval Devices

A. Exemplary Tissue Retrieval Device with Translatable Rod

Figure 2:
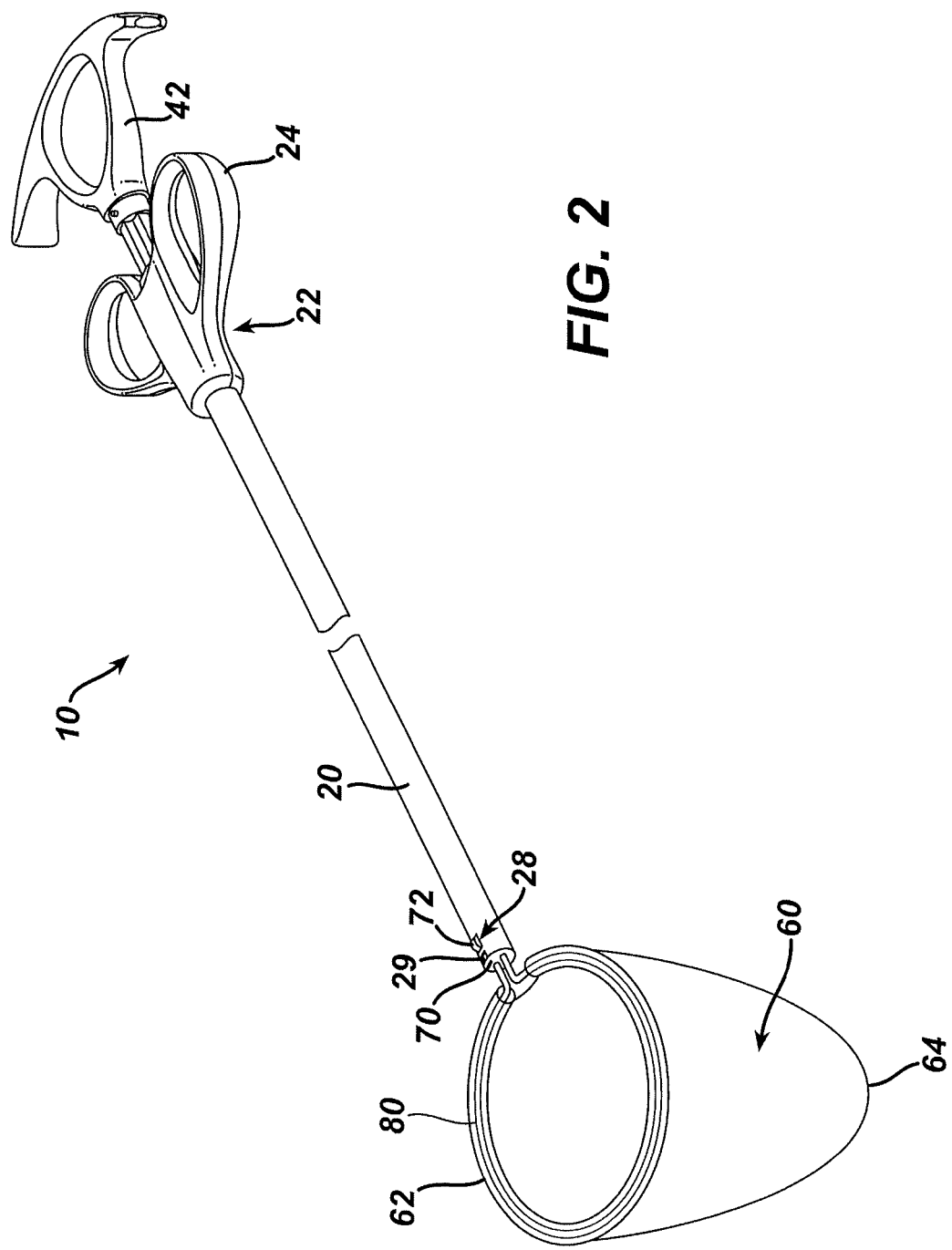
FIG. 2 is a perspective view of the tissue retrieval device of FIG. 1, with the retrieval bag in a deployed position.
Figure 3:
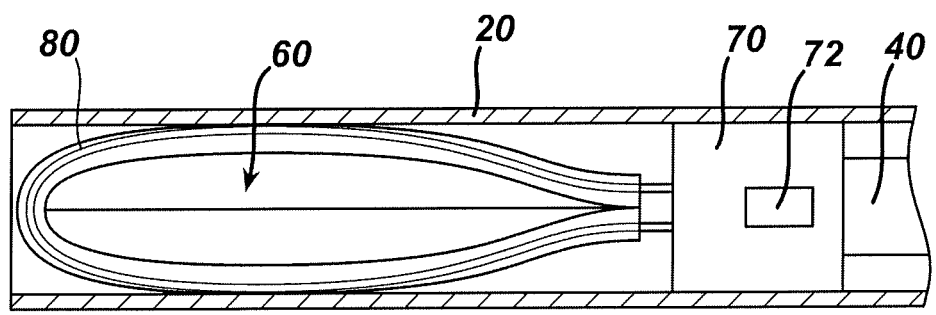
FIG. 3 is a top view of the distal end of the tissue retrieval device of FIG. 1, with the retrieval bag in the retracted position and with the introducer tube shown in cross section.
Figure 4:
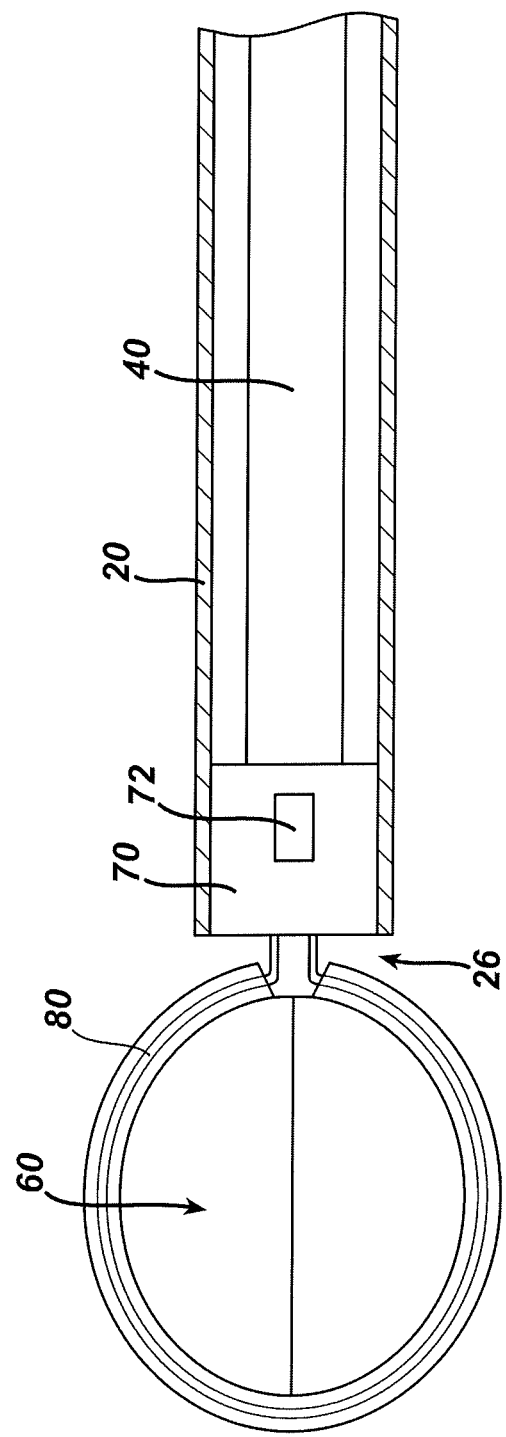
FIG. 4 is a top view of the distal end of the tissue retrieval device of FIG. 1, with the retrieval bag in the deployed position and with the introducer tube shown in cross section.

FIGS. 1-4 show an exemplary tissue retrieval device (10). In this example, tissue retrieval device (10) comprises an elongate introducer tube (20), a handle (22) secured to the proximal end of introducer tube (20), an actuating rod (40), and a thumb ring (42) secured to the proximal end of actuating rod (40). Handle (22) comprises a pair of finger grips (24). As will be described in greater detail below, actuating rod (40) is slidable within the hollow interior of introducer tube (20) to selectively deploy a tissue retrieval bag (60) from introducer tube (20). In particular, with actuating rod (40) in a proximal position as shown in FIGS. 1 and 3, a user may insert their thumb in thumb ring (42), and insert their index and middle fingers in finger grips (24), then advance thumb ring (42) distally toward finger grips (24) to translate actuating rod (40) distally to a distal position as shown in FIGS. 2 and 4.

In the present example introducer tube (20) is formed of metal; while handle (22), actuating rod (40), and thumb ring (42) are formed of plastic. However, it should be understood that any suitable material or combination of materials may be used to form these components and other components described herein. Introducer tube (20) has an open distal end (26) and a side aperture (28) just proximal to open distal end (26). Introducer tube (20) of the present example is sized such that introducer tube (20) may be introduced to a surgical site through a trocar or other type of device. By way of example only, the outer diameter of introducer tube (20) may be between approximately 5 mm (inclusive) and approximately 15 mm (inclusive). Alternatively, introducer tube (20) may have any other suitable dimension.

As shown in FIGS. 3-4, a distal plug (70) is secured to the distal end of actuating rod (40). Distal plug (70) is thus translatable from a proximal position as shown in FIG. 3 to a distal position as shown in FIG. 4 by translating actuating rod (40) distally as described above. Distal plug (70) includes a resilient tab (72) that extends upwardly from distal plug (70). Resilient tab (72) is resiliently biased to extend upwardly from distal plug (70), but is movable downwardly toward distal plug (70) in order to allow distal plug (70) to fit within and translate within introducer tube (20). However, once distal plug (70) reaches the distal position shown in FIGS. 2 and 4, resilient tab (72) is configured to "snap into" side aperture (28) of introducer tube (20), such that at least a portion of resilient tab (72) protrudes into side aperture (28). With resilient tab (72) so engaged with side aperture (28), the longitudinal position of distal plug (70) may be substantially secured. In other words, engagement between resilient tab (72) and side aperture (28) may substantially prevent proximal movement of distal plug (70) once distal plug (70) has reached a distal position. Engagement between actuating rod (40) and distal plug (70) may also prevent proximal movement of actuating rod (40) when distal plug (70) has reached the distal position. Distal plug (70) may also include a recess below resilient tab (72), which may provide clearance for resilient tab (72) to deflect downwardly when distal plug (70) is proximal to the distal position shown in FIGS. 2 and 4. Such downward deflection on resilient tab (72) may be provided by the inner diameter of introducer tube (20) when distal plug (70) is proximal to the distal position shown in FIGS. 2 and 4.

One or more indentations (29) formed at distal end (26) of introducer tube (20) may also restrict distal positioning of distal plug (70). Such restriction of distal positioning of distal plug (70) may also restrict distal positioning of actuating rod (40). In addition or in the alternative, a feature on a proximal portion of actuating rod (40) may engage handle (22) when actuating rod (40) reaches a certain distal position, to arrest further distal translation of actuating rod (40) at a selected longitudinal position. In some such versions, distal plug (70) may even be omitted. For instance, resilient hoop member (80) may be integrally secured to actuating rod (40), such that a feature located near the proximal end of tissue retrieval device (10) that arrests distal translation of actuating rod (40) (e.g., by arresting distal motion of thumb ring (42), etc.) may effectively also arrest distal positioning of resilient hoop member (80). In addition or in the alternative, distal plug (70) and side aperture (28) may be located substantially proximal to the locations of these features shown in FIGS. 1-4.

As shown in FIGS. 2-4, a resilient hoop member (80) extends distally from distal plug (70). Resilient hoop member (80) is resiliently biased to assume an outwardly expanded circular or elliptical configuration as shown in FIGS. 2 and 4. Alternatively, resilient hoop member (80) may be resiliently biased to assume any other suitable configuration. Resilient hoop member (80) has flexibility permitting resilient hoop member (80) to compress and deformably fit within introducer tube (20) as shown in FIGS. 1 and 3. A secure attachment between resilient hoop member (80) and distal plug (70) provides unitary translation of resilient hoop member (80) and distal plug (70) relative to introducer tube (20). In addition, a secure attachment between actuating rod (40) and distal plug (70) provides unitary translation of actuating rod (40) and distal plug (70). Thus, resilient hoop member (80) may be advanced from a proximal position as shown in FIG. 3 to a distal position as shown in FIG. 4 by advancing thumb ring (42) distally toward handle (22) as described above. Such distal advancement of resilient hoop member (80) moves resilient hoop member (80) from a proximal position where it is located within introducer tube (20) to a distal position where it protrudes from open distal end (26) of introducer tube (20).

Resilient hoop member (80) may be formed of any suitable material or combination of materials, including but not limited to metal (e.g., stainless steel, nitinol, steel spring alloys, copper spring alloys, etc.), plastic, and/or metal reinforced plastic. In addition, while resilient hoop member (80) is formed as a single unitary piece, resilient hoop member (80) may alternatively be formed of any other suitable number of pieces. By way of example only, resilient hoop member (80) may be formed of two separate arms that together provide a configuration that is substantially similar to the configuration shown for resilient hoop member (80), except that the two separate arms are separated at a region corresponding to the distal-most part of resilient hoop member (80). Other suitable variations of resilient hoop member (80) will be apparent to those of ordinary skill in the art in view of the teachings herein. By way of example only, resilient hoop member (80) may be readily substituted with any bag frame component or support structure disclosed in any of the patents or patent applications cited herein. Similarly, tissue retrieval device (10) may readily incorporate any of the various bag deployment mechanisms disclosed in any of the patents or patent applications cited herein. Various suitable ways in which such alternative bag frames, support structures, deployment mechanisms, and/or other teachings in any of the patents or patent applications cited herein may be incorporated into tissue retrieval device (10) will be apparent to those of ordinary skill in the art.

Retrieval bag (60) has an open top portion (62) and a closed bottom portion (64). Open top portion (62) is sized to receive a tissue specimen. Top portion (62) is secured to resilient hoop member (80) in the present example. For instance, resilient hoop member (80) may be fed through sleeves, slots, pockets, loops, slits, etc., or one or more other features near the top opening of retrieval bag (60). The engagement between retrieval bag (60) and resilient hoop member (80) is such that retrieval bag (60) translates substantially unitarily with resilient hoop member (80) relative to introducer tube (20). Thus, retrieval bag (60) may be advanced from a proximal position as shown in FIGS. 1 and 3 to a distal position as shown in FIGS. 2 and 4 by advancing thumb ring (42) distally toward handle (22) as described above. In addition, the engagement between retrieval bag (60) and resilient hoop member (80) is such that resilient hoop member (80) substantially opens the top of retrieval bag (60) when resilient hoop member (80) reaches the expanded configuration shown in FIGS. 2 and 4. While resilient hoop member (80) is flexible enough to compressibly fit within introducer tube (20), resilient hoop member (80) has sufficient rigidity to substantially support retrieval bag (60) when resilient hoop member (80) and retrieval bag (60) protrude from open distal end (26) of introducer tube (20).

Retrieval bag (60) may have any suitable configuration when retrieval bag (60) is positioned within introducer tube (20). For instance, retrieval bag (60) may be rolled up, folded up, wadded up, or have any other suitable configuration within introducer tube (20). Various suitable configurations for retrieval bag (60) within introducer tube (20) will be described in greater detail below, while other suitable configurations for retrieval bag (60) within introducer tube (20) will be apparent to those of ordinary skill in the art in view of the teachings herein. When retrieval bag (60) has been advanced from a proximal position as shown in FIGS. 1 and 3 to a distal position as shown in FIGS. 2 and 4, a separate instrument (e.g., conventional tissue graspers, etc.) may be used to assist in unfurling retrieval bag (60). In addition or in the alternative, the material properties of retrieval bag (60), some other feature(s) of retrieval bag (60), and/or gravity may cause retrieval bag (60) to at least substantially unfurl on its own once it has been deployed from introducer tube (20). With retrieval bag (60) deployed and opened as shown in FIGS. 2 and 4, a surgeon may place tissue samples or specimens, etc. (e.g., patient's gall bladder, etc.) within retrieval bag (60) for subsequent removal of such tissue samples or specimens, etc. from the patient.

In some versions, tissue retrieval device (10) may be configured such that retrieval bag (60) is removable from resilient hoop member (80) (e.g., while these components are still within the patient, etc.). Some such versions facilitate removal of retrieval bag (60) separate from removal of the other components of the tissue retrieval device (10) from the patient. For instance, in some versions tissue retrieval device (10) may include a closure string (not shown) connected to retrieval bag (60) and having a slipknot attachment to actuating rod (40). Pulling the slipknot loose from actuating rod (40) and then retracting actuating rod (40) proximally may permit detachment of retrieval bag (60) and the closure string from the other components of specimen retrieval device (10). For instance, actuating rod (40) may be fully withdrawn from introducer tube (20) and a free end of the closure string may protrude from the proximal end of introducer tube (20). In some such versions, a user may pull the closure string to close retrieval bag (60). For instance, the closure string may be engaged with retrieval bag (60) similar to a purse string. By way of example only, such a closure mechanism may be configured in accordance with the teachings of U.S. Pat. No. 6,409,733, entitled "Specimen Retrieval Bag," issued Jun. 25, 2002, the disclosure of which is incorporated by reference herein. In some such versions, retrieval bag (60) is perforated in a region between a closure string and the region where retrieval bag (60) is coupled with resilient hoop member (80). Such perforation may permit retrieval bag (60) to be separated from hoop member (80) without compromising engagement between the closure string and retrieval bag (60). In addition or in the alternative, hoop member (80) may have a break in it or be breakable to allow retrieval bag (60) to be pulled off of hoop member (80). Other suitable ways in which retrieval bag (60) may be removable from hoop member (80) and/or closed will be apparent to those of ordinary skill in the art in view of the teachings herein.

A closed retrieval bag (60) containing tissue may be removed through the same trocar through which introducer tube (20) was inserted. In particular, a closed retrieval bag (60) containing tissue may be removed through the trocar at the same time introducer tube (20) is removed from the trocar. Alternatively, introducer tube (20) may be removed from the trocar first, then the closed retrieval bag (60) containing tissue may be removed through the trocar. As yet another merely illustrative alternative, the closed retrieval bag (60) containing tissue may be removed from the patient after introducer tube (20) and the trocar have been removed from the patient. In other words, the closed retrieval bag (60) containing tissue may be removed directly through the incision through which the trocar had been previously inserted. In any of these scenarios, a protruding closure string may be used to remove retrieval bag (60) from the patient. Alternatively, retrieval bag (60) may be removed from the patient in any other suitable fashion.

In some versions, actuating rod (40) may comprise features operable with other features of introducer tube (20) or other components to prevent inadvertent retraction of actuating rod (40) during deployment of retrieval bag (60). For example, actuating rod (40) may include a one way ratcheting mechanism as described in U.S. Pat. No. 6,409,733, entitled "Specimen Retrieval Bag," issued Jun. 25, 2002, the disclosure of which is incorporated by reference herein. Other ways in which inadvertent retraction of actuating rod (40) may be avoided through various features of tissue retrieval device (10) will be apparent to those of ordinary skill in the art in view of the teachings herein. Similarly, other various suitable components, features, configurations, and functionalities of tissue retrieval device (10) will be apparent to those of ordinary skill in the art in view of the teachings herein.

B. Exemplary Tissue Retrieval Device with Retractable Sheath

Figure 5:
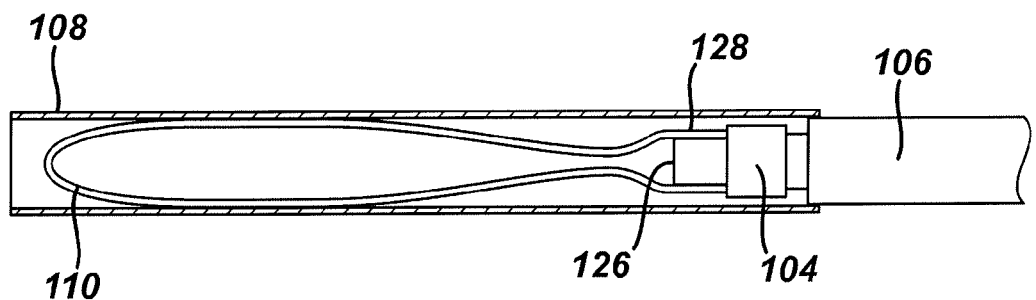
FIG. 5 is a top view of the distal end of another exemplary alternative tissue retrieval device, with a sheath in a distal position and shown in cross section, and with a retrieval bag omitted.
Figure 6:
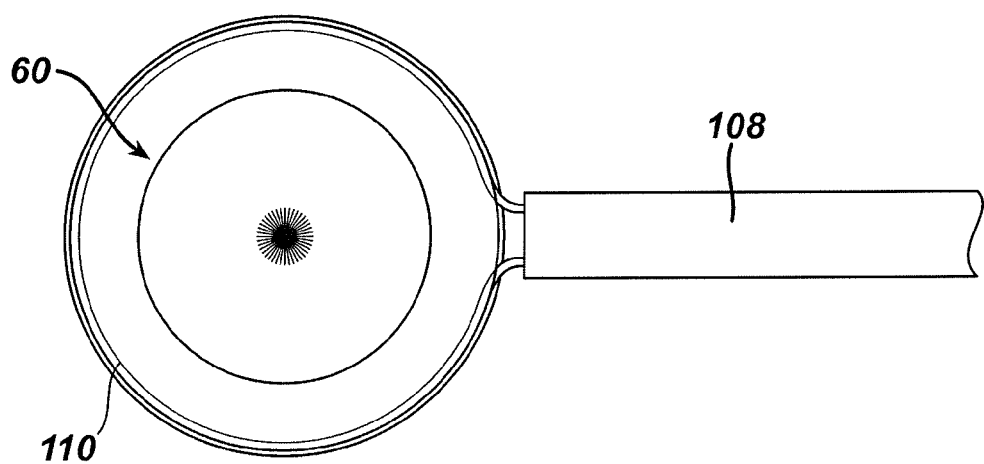
FIG. 6 is a top view of the distal end of the tissue retrieval device of FIG. 5, with the sheath in a proximal position.

FIGS. 5-6 show exemplary alternative features that may be incorporated into a tissue retrieval device such as tissue retrieval device (10). In particular, this alternative tissue retrieval device includes a rod (104), an introducer tube (106), a sheath (108), a resilient hoop (110), and a retrieval bag (60). Rod (104) is fixedly positioned within introducer tube (106) in the present example. However, in some other versions, rod (104) may me configured to reciprocate within introducer tube (106) (e.g., like rod (40) of tissue retrieval device (10) described above, etc.). Sheath (108) is configured to translate relative to introducer tube (106). In particular, and as will also be described in greater detail below, sheath (108) is translatable from a distal position (FIG. 5) to a proximal position (FIG. 6). Together, introducer tube (106) and sheath (108) are configured to fit within the insertion passageway defined by a device such as a trocar. By way of example only, introducer tube (106) and sheath (108) may present an outer diameter that is between approximately 5 mm (inclusive) and approximately 15 mm (inclusive). Alternatively, these components may have any other suitable dimensions. Resilient hoop (110) carries retrieval bag (60), and is resiliently biased to expand from a compressed configuration (FIG. 5) to an expanded configuration (FIG. 6), as will also be described in greater detail below.

FIG. 5 shows the alternative specimen retrieval instrument of the present example in an undeployed configuration. In this configuration, sheath (108) is in a distal position, substantially enclosing resilient resilient hoop (110) and retrieval bag (60). In this configuration, the specimen retrieval instrument is ready to be inserted within a patient. By way of example only, the specimen retrieval instrument may be inserted into a patient via a trocar or other type of access port device, via an incision, via a natural orifice, and/or in any other suitable fashion. Introducer tube (106) has a substantially cylindraceous configuration in the present example However, it should be understood that introducer tube (106) may have any suitable configuration. In addition, it should be understood that any suitable type of handle assembly may be provided at the proximal end of introducer tube (106) and/or sheath (108). By way of example only, such a handle assembly may have one or more finger grips, thumb rings, or any other suitable structures, features, or configurations. Such a handle assembly may be configured to facilitate proximal translation of sheath (108) relative to introducer tube (106). In addition or in the alternative, one or more cables, strings, rods, or other features may be operable to provide proximal translation of sheath (108) relative to introducer tube (106).

FIG. 6 shows the alternative specimen retrieval instrument of the present example in a deployed configuration. In this configuration, sheath (108) is in a proximal position, substantially revealing resilient resilient hoop (110) and retrieval bag (60). In the present example, the specimen retrieval instrument is transitioned from the undeployed configuration to the deployed configuration after the distal end of the specimen retrieval instrument has been inserted within a patient. To transition the specimen retrieval instrument from the undeployed configuration to the deployed configuration, sheath (108) is retracted proximally relative to introducer tube (106). It should be understood that such proximal retraction of sheath (108) may be accomplished in a variety of ways. By way of example only, sheath (108) may have a length selected such that a proximal portion of sheath (108) protrudes proximally relative to a trocar or other access port when the distal end of the specimen retrieval instrument is inserted in a patient. Thus, such a proximal portion of sheath (108) may be manipulated by a surgeon or other user externally relative to the patient during a surgical procedure. A handle, grip, or other structural feature may be provided at the proximal end of sheath (108) to facilitate such extracorporeal manipulability of sheath (108). In addition or in the alternative, a string, cable, or other feature may be coupled with sheath (108) and may be operable to retract sheath (108) proximally. In addition or in the alternative, a feature that is operable to retract sheath (108) proximally may extend within the interior of introducer tube (106), in addition to or as an alternative to extending along the exterior of introducer tube (106).

In some alternative versions, sheath (108) is removable from introducer tube (106) by pulling sheath (108) off of introducer tube (106) in a distal direction; rather than providing proximal retractability of sheath (108). By way of example only, sheath (108) may be configured like a sleeve or sock, and a separate instrument (e.g., conventional tissue graspers, etc.) may be used to pull sheath (108) distally off of resilient resilient hoop (110) and retrieval bag (60). In addition or in the alternative, sheath (108) may have a perforation or other weakening feature that may be breached to remove sheath (108) by tearing sheath (108) away from introducer tube (106). As yet another merely illustrative alternative, sheath (108) may be formed of an environmentally sensitive material. For instance, sheath (108) may be configured to dissolve or substantially weaken in the presence of bodily fluid, certain temperatures, or other environmental parameters that may be associated with the interior of a patient. Still other various ways in which sheath (108) may be configured and/or operable will be apparent to those of ordinary skill in the art in view of the teachings herein. Furthermore, sheath (108) may even be omitted in some versions.

Retrieval bag (60) is substantially identical to retrieval bag (60) described above in the context of specimen retrieval instrument (10). In addition, engagement between retrieval bag (60) and resilient hoop (110) is substantially identical to the engagement between retrieval bag (60) and resilient hoop (80) described above in the context of specimen retrieval instrument (10). Alternatively, these components may have any other suitable configurations and relationships.

As noted above, resilient hoop (110) is resiliently biased to maintain a substantially circular shape when not constricted by other components. Of course, resilient hoop (110) may be resiliently biased to maintain any other suitable shape. As shown in FIG. 5, resilient hoop (110) is connected to distal end (126) of rod (104). In the present example, the connection of resilient hoop (110) to rod (104) is achieved by resilient hoop (110) having parallel proximal ends (128) that secure to respective sides of distal end 126 of rod (104) by the use of securing pins (not shown) or other suitable attachment means. As noted above, rod (104) is fixedly positioned within introducer tube (106) in the present example. Accordingly, resilient hoop (110) and retrieval bag (60) are fixedly positioned relative to introducer tube (106) in the present example. However, it should be understood that these components may be substituted with various other components or structures; and that these components may have a variety of alternative relationships with each other. By way of example only, in some versions rod (104) is configured to translate relative to introducer tube (106), much like translation of rod (40) relative to introducer tube (20) described above in the context of specimen retrieval instrument (10), with resilient hoop (110) and retrieval bag (60) being locatable within the hollow interior defined by introducer tube (106).

In use, the alternative specimen retrieval instrument of the present example may initially have the arrangement shown in FIG. 5, where sheath (108) is at a distal position. In this arrangement, the distal portion of the specimen retrieval instrument 100 may be inserted within a patient through a suitable incision opening or access port created by a trocar or some other device. Once positioned within the patient, sheath (108) may be retracted proximally. This action reveals resilient hoop (110) and retrieval bag (60). With resilient hoop (110) being so freed from the confines of sheath (108), the resilient bias of resilient hoop (110) causes loop to expand to the configuration shown in FIG. 6, thereby opening retrieval bag (60). Once retrieval bag (60) has been opened, one or more tissue specimens, etc., may be placed within retrieval bag (60). Once a specimen has been placed within retrieval bag (60), sheath (108) may be advanced distally relative to introducer tube (106), with introducer tube (106) maintaining a substantially constant position relative to the patient (or introducer tube (106) may be retracted proximally relative to sheath (108), with sheath (108) maintaining a substantially constant position relative to the patient). Such a motion may thus cause sheath (108) to at least substantially envelop resilient hoop (110) once again. In particular, such engagement between sheath (108) and resilient hoop (110) may cause resilient hoop (110) to transition back toward a substantially collapsed configuration. Overcoming the resilient bias of resilient hoop (110) in this way may permits resilient hoop (110) and retrieval bag (60) to close, and in some versions for a proximal portion of resilient hoop (110) to be constrained within a distal portion of sheath (108). With retrieval bag (60) closed, the specimen retrieval instrument is now ready to be removed from the patient. Of course, there does not necessarily have to be any relative movement between sheath (108) and introducer tube (106) after a specimen has been placed in retrieval bag (60) and before the specimen retrieval instrument is removed from the patient.

In some versions, the alternative specimen retrieval instrument of the present example is configured such that retrieval bag (60) may be removed from the specimen retrieval instrument while retrieval bag (60) is within the patient. Some such versions facilitate removal of retrieval bag (60) separate from removal of the other components of the specimen retrieval instrument. In some versions, this may be accomplished by, among other ways, retrieval bag (60) being removable from resilient hoop (110). For instance, in some versions the specimen retrieval instrument may include a closure string as described above and as taught in U.S. Pat. No. 6,409,733, entitled "Specimen Retrieval Bag," issued Jun. 25, 2002, which is incorporated herein by reference. Other suitable ways in which retrieval bag (60) may be removable from hoop (110) and/or closed will be apparent to those of ordinary skill in the art in view of the teachings herein. In addition, various suitable ways in which a retrieval bag (60) may be removed from a patient will be apparent to those of ordinary skill in the art in view of the teachings herein.

In some versions, modifications may include rod (104) or introducer tube (106) having features operable with features of sheath (108) or other components to prevent inadvertent retraction of sheath (108) and premature opening of resilient hoop (110) and retrieval bag (60). For example, rod (104) may include a lock or stop that may be released once a user is ready to open resilient hoop (110) and retrieval bag (60). Still in other versions, modifications may include rod (104) having features operable with features of sheath (108) or other components to prevent inadvertent advancement of sheath (108) after initial deployment of resilient hoop (110) and opening of retrieval bag (60). For example, rod (104) may be associated with a resilient tab configured to engage a corresponding opening in a sidewall of sheath (108) upon deployment of resilient hoop (110). The engagement between the resilient tab and the opening in the sidewall of sheath (108) may act as a locking mechanism that prevents inadvertent advancement of sheath (108), and therefore inadvertent premature closure of resilient hoop (110) and retrieval bag (60). Other ways in which inadvertent retraction and/or advancement of sheath (108) may be avoided through various features of a specimen retrieval instrument will be apparent to those of ordinary skill in the art in view of the teachings herein.

C. Exemplary Tissue Retrieval Device with Staged Actuation

FIGS. 7-10 show an example of how actuation of a tissue retrieval bag (260) may be staged to provide selectability of the size of tissue retrieval bag (260) as tissue retrieval bag (260) is being deployed. In this example, tissue retrieval bag (260) is secured to a pair of resilient arms (280). Resilient arms (280) are secured to the distal end (242) of an actuating rod (240). Actuating rod (240) is slidably disposed within an introducer tube (220), such that actuating rod (240) may be advanced distally within introducer tube (220). In particular, actuating rod (240) may be translated distally from a proximal position (FIG. 7) to a first distal position (FIG. 8); then translated further distally to a second distal position (FIGS. 9-10). In some versions, actuating rod (240) may also be retracted proximally within introducer tube (220) after actuating rod (240) has reached a distal position. Introducer tube (220) and actuating rod (240) may be configured and operable in accordance with the above teachings relating to introducer tube (20) and actuating rod (40). Alternatively, introducer tube (220) and actuating rod (240) may have any other suitable components, features, configurations, or operabilities.

Figure 7:
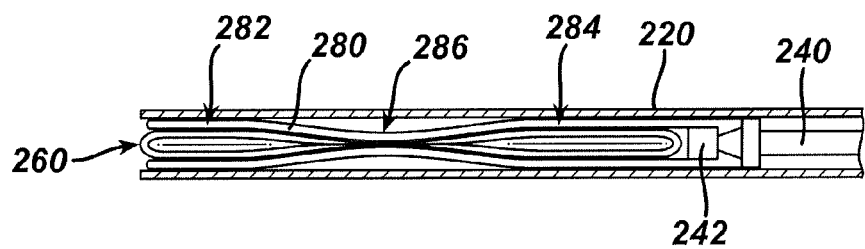
FIG. 7 is a top view of the distal end of another exemplary tissue retrieval device, with a retrieval bag in a retracted position, and with an introducer tube shown in cross section.
Figure 8:
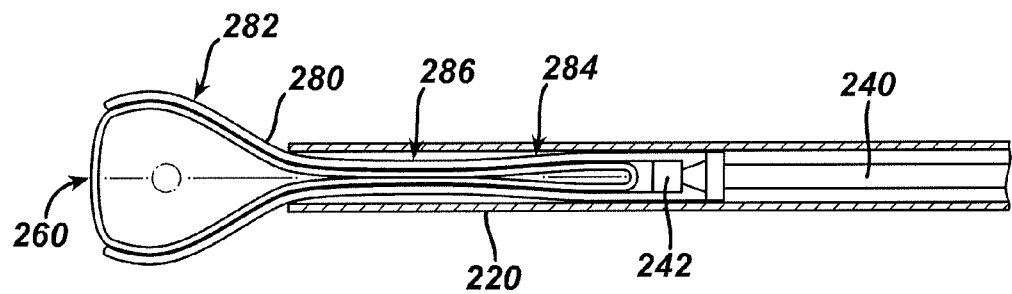
FIG. 8 is a top view of the distal end of the tissue retrieval device of FIG. 7, with the retrieval bag in a first deployed position, and with the introducer tube shown in cross section.

As noted above, resilient arms (280) are secured to distal end (242) of actuating rod (240); and retrieval bag (260) is secured to resilient arms (280). Resilient arms (280) are resiliently biased to assume an hourglass-like configuration as shown in FIG. 9. In this configuration, each resilient arm (280) has a distal convex portion (282), a proximal convex portion (284), and a concave portion (286) providing a transition between convex portions (282, 284). Resilient arms (280) may be formed of any suitable material or combination of materials, including but not limited to metal (e.g., stainless steel, nitinol, steel spring alloys, copper spring alloys, etc.), plastic, and/or metal reinforced plastic. Resilient arms (280) are also flexible enough to substantially straighten out when resilient arms (280) are retracted within the hollow interior of introducer tube (220). Resilient arms (280) are nevertheless rigid enough to support retrieval bag (260) when a tissue specimen (290) is placed in retrieval bag (260) as shown in FIG. 10. By way of example only, resilient arms (280) may be formed as vertically oriented strips that are configured to flex along a substantially horizontal plane yet that are also configured to resist flexing along a substantially vertical plane. While resilient arms (280) are formed as separate components in the present example, it should be understood that resilient arms (280) may have a variety of other configurations. For instance, resilient arms (280) may instead be formed as a single hoop, similar to resilient hoop member (80), etc. Other suitable configurations for resilient arms (280) will be apparent to those of ordinary skill in the art in view of the teachings herein The configuration of resilient arms (280) and the resilient properties of resilient arms (280) in the present example provide staged opening of retrieval bag (260) based on the longitudinal position of actuating rod (240) relative to introducer tube (220). In particular, as shown in FIG. 7, retrieval bag (260) may be initially closed and retracted within introducer tube (220) when actuating rod (240) is at a proximal position. At this stage, introducer tube (220) may be inserted into a patient via a trocar, incision, or some other type of entry as described herein. When actuating rod (240) is advanced to a first distal position as shown in FIG. 8, resilient arms (280) and retrieval bag (260) partially emerge from the open distal end of introducer tube (220). In particular, resilient arms (280) are advanced to a position sufficient to expose distal convex portion (282), with proximal convex portion (284) remaining within introducer tube (220). Despite this partial deployment of resilient arms (280) and retrieval bag (260), retrieval bag (260) is still opened sufficiently to allow a relatively small tissue specimen to be placed in retrieval bag (260). In some settings, it is not necessary or otherwise desirable to open retrieval bag (260) any further than the degree of opening provided by this first deployment stage. In some such settings, the surgeon or other use may refrain from advancing actuating rod (240) any further distally, and may close retrieval bag (260) and/or remove retrieval bag (260) from resilient arms (280) for removal of the tissue specimen contained in retrieval bag (260). Such closing and/or removal may include the use of a closure string and/or may otherwise be performed in accordance with the related teachings discussed above in the context of tissue retrieval device (10). Alternatively, such closing and/or removal may be provided in any other suitable fashion as will be apparent to those of ordinary skill in the art in view of the teachings herein.

In some settings, the degree of retrieval bag (260) opening provided by the above described first deployment stage is not sufficient for a tissue specimen (290) to be placed in retrieval bag (260). In some such settings, actuating rod (240) may be advanced further distally to the position shown in FIG. 9. In this position, resilient arms (280) and retrieval bag (260) more fully emerge from the open distal end of introducer tube (220). In particular, resilient arms (280) are advanced to a position sufficient to expose distal convex portion (282), proximal convex portion (284), and concave portion (286). With such lengths of resilient arms (280) being exposed relative to introducer tube (220), retrieval bag (260) is opened to a greater degree than is shown in FIG. 8, allowing retrieval bag (260) to more easily accept a relatively larger tissue specimen (290) as shown in FIG. 10. As is also shown in FIG. 10, resilient arms (280) of the present example are configured to buckle outwardly. As a result of such buckling, concave portion (286) of each resilient arm (280) becomes convex, providing a substantially continuous curve between convex portions (282, 284). Of course, such buckling may be absent in some versions, such that a tissue specimen is placed in retrieval bag (260) with resilient arms (280) substantially maintaining the configuration shown in FIG. 9.

In some versions, actuating rod (240) is advanced distally relative to introducer tube (220) by advancing a thumb ring toward finger grips in a manner similar to that described above in the context of tissue retrieval device (10). In some other versions, introducer tube (220) is provided as a retractable sheath, such that introducer tube (220) is retracted proximally relative to a patient while the position of actuating rod (240) relative to the patient remains substantially constant. Further merely illustrative examples of instruments that may be used to deploy resilient arms (280) and retrieval bag (260) are shown in FIGS. 11-13 and are described in greater detail below; while still other examples of instruments that may be used to deploy resilient arms (280) and retrieval bag (260) will be apparent to those of ordinary skill in the art in view of the teachings herein.

Figure 11:
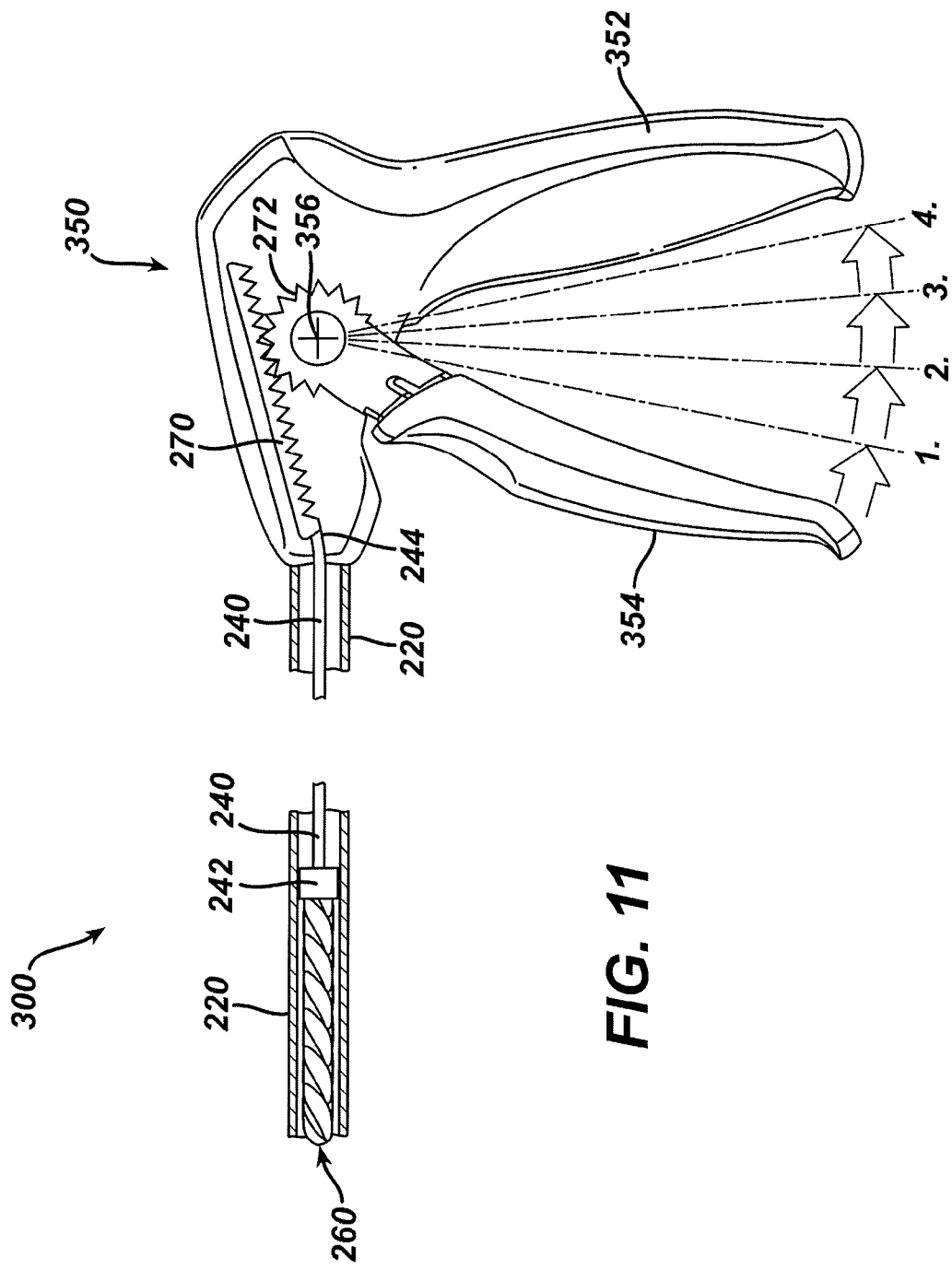
FIG. 11 is a side view of another exemplary tissue retrieval device, providing staged actuation of a tissue retrieval bag, with an introducer tube shown in cross section, and with a portion of the handle omitted.

FIG. 11 depicts an exemplary tissue retrieval device (300) that may be used to deploy resilient arms (280) and retrieval bag (260) as described above. In this example, tissue retrieval device (300) comprises a handle portion (350), which comprises a pistol grip (352) and a trigger handle (354). Trigger handle (354) is pivotally coupled relative to pistol grip (352), such that trigger handle (354) is selectively pivotable toward pistol grip (352), about a pivot pin (356). Introducer tube (220) extends distally from handle portion (350). As described above, actuating rod (240) is translatable within introducer tube (220). In the present example, a rack (270) is secured to the proximal end (244) of actuating rod (240). Rack (270) is engaged with a pinion (272), which is integral with and is presented by trigger handle (354). The engagement between rack (270) and pinion (272) is such that, as trigger handle (354) is rotated about pivot pin (356) toward pistol grip (352), rack (270) is advanced distally. The engagement between rack (270) and actuating rod (240) is such that actuating rod (240) advances distally when rack (270) is advanced distally. Accordingly, it should be understood that resilient arms (280) and retrieval bag (260) may be selectively deployed by rotating trigger handle (354) about pivot pin (356) toward pistol grip (352), such as by squeezing trigger handle (354) and pistol grip (352) together.

The surgeon or other user may selectively vary the degree to which retrieval bag (260) is opened by selectively varying the degree to which trigger handle (354) is rotated about pivot pin (356) toward pistol grip (352). For instance, to transition retrieval bag (260) from the position and configuration shown in FIG. 7 to the position and configuration shown in FIG. 8, the surgeon or other user may rotate trigger handle (354) about pivot pin (356) part-way toward pistol grip (352). Tissue retrieval device (300) may include one or more selective locking features (e.g., ratcheting mechanism, etc.) allowing the rotational position of trigger handle (354) relative to pistol grip (352) to be selectively fixed, thereby providing selective fixation of the degree to which retrieval bag (260) is opened and deployed. Alternatively, the surgeon or other user may simply hold trigger handle (354) in a selected rotational position relative to pistol grip (352) to maintain a selected degree of opening/deployment of retrieval bag (260). In the present example, tissue retrieval device (300) is configured such that full opening and deployment of retrieval bag (260) as shown in FIG. 10 may be accomplished by completing a single stroke of rotating trigger handle (354) about pivot pin (356) relative to pistol grip (352). Alternatively, tissue retrieval device (300) may be configured to require multiple strokes of rotating trigger handle (354) about pivot pin (356) relative to pistol grip (352) in order to achieve full opening and deployment of retrieval bag (260) as shown in FIG. 10.

Figure 12:
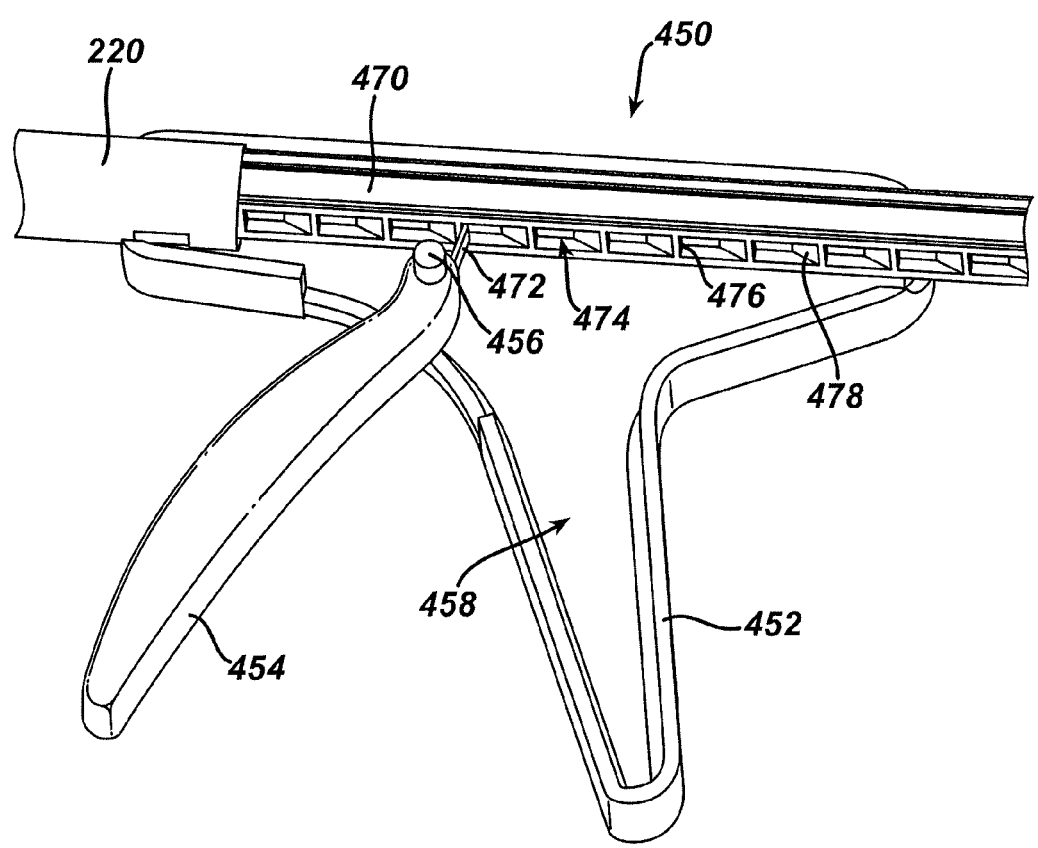
FIG. 12 is a perspective view of an exemplary alternative handle portion for the tissue retrieval device of FIG. 11, with a portion of the handle omitted.
Figure 13:
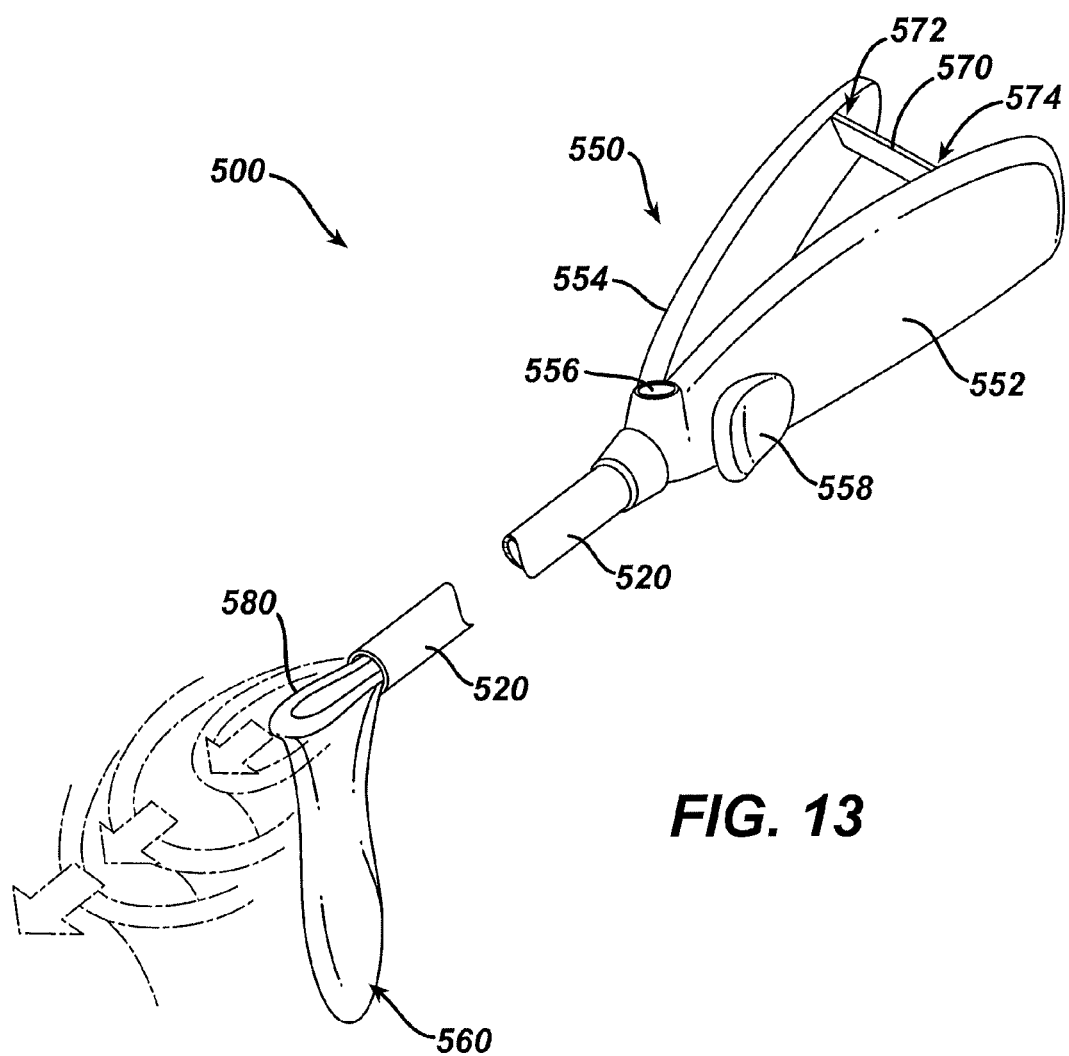
FIG. 13 is a perspective view of another exemplary tissue retrieval device, providing staged actuation of a tissue retrieval bag.
Figure 14:
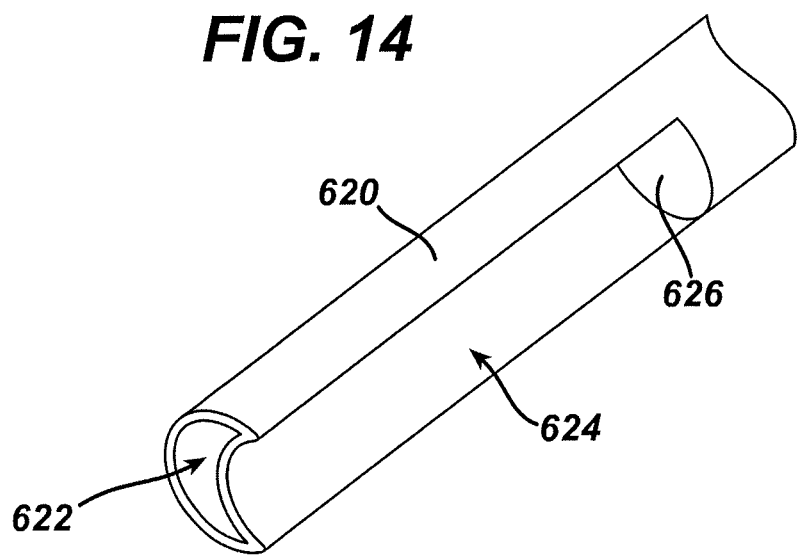
FIG. 14 is a perspective view of the distal end of an introducer tube of an exemplary alternative tissue retrieval device.

FIG. 12 depicts an exemplary variation of tissue retrieval device (300), in which multiple strokes are required in order to achieve full opening and deployment of retrieval bag (260) as shown in FIG. 10. Like tissue retrieval device (300) described above, a handle portion (450) is secured to introducer tube (220). In addition, this handle portion (450) also includes a pistol grip (452) and a trigger handle (454). While only one half (458) of the housing of handle portion (450) is shown in FIG. 12, it should be understood that the other half may look substantially identical to the housing half (458) shown. Trigger handle (454) is pivotable about a pivot pin (456), toward pistol grip (452).

In this example, an actuating member (470) is secured to the proximal end (244) of actuating rod (240). A pawl (472) is integral with and presented by trigger handle (454). The underside of actuating member (470) includes a plurality of recesses (474), which are configured to receive pawl (472). Each recess (474) includes a front wall (476) and a rear wall (478). Each front wall (476) is substantially vertical (e.g., perpendicular to the longitudinal axis defined by actuating rod (240) and actuating member (470), etc.) in the present example; while each rear wall (476) is substantially ramped (e.g., obliquely angled relative to the longitudinal axis defined by actuating rod (240) and actuating member (470), etc.). Trigger handle (454) is operable to advance actuating member (470) incrementally in this example. In particular, the engagement between pawl (472) and actuating member (470) is such that pawl (472) advances actuating member (470) by one recess (474) for each stroke of trigger handle (454). As trigger handle (454) is rotated about pivot pin (456) toward pistol grip (452) (e.g., in the counter-clockwise direction in the view shown in FIG. 12), pawl (472) pushes on front wall (476) of whichever recess (474) pawl (472) is disposed in. This causes actuating member (470) to advance distally by a certain increment, which causes actuating rod (240) to advance distally in a certain increment, which in turn causes resilient arms (280) and retrieval bag (260) to be exposed relative to the open distal end of introducer tube (220) to a certain incremental degree.

Once trigger handle (454) has been rotated about pivot pin (456) toward pistol grip (452) as far as it can go (e.g., until trigger handle (454) contacts pistol grip (452), etc.), trigger handle (454) may be rotated in the opposite direction (e.g., in the clockwise direction in the view shown in FIG. 12) to reset trigger handle (454). During this opposite rotation, pawl (472) may "ride" rear wall (478) of recess (474) to allow pawl (472) to clear recess (474) and to thereby allow pawl (472) to register to the next adjacent recess (474). In some versions, handle portion (450) includes one or more springs or other types of resilient members that are configured to bias trigger handle (454) to a rotational position where trigger handle (454) is separated from pistol grip (452). In some such versions, the surgeon or other user need only release trigger handle (454) to allow trigger handle (454) to rotate away from pistol grip (452) after a first actuation stroke, to thereby register pawl (472) to the next adjacent recess (474). This process of squeezing trigger handle (454) toward pistol grip (452) and then releasing trigger handle (454) or otherwise rotating trigger handle (454) away from pistol grip (452) may be repeated any desired number of times in order to incrementally advance actuating member (470), actuating rod (240), resilient arms (280), and retrieval bag (260) to a selected deployment position relative to introducer tube (220). It should be understood that, in the present example, full opening and deployment of retrieval bag (260) as shown in FIG. 10 may be accomplished by completing a several strokes of rotating trigger handle (454) about pivot pin (456) relative to pistol grip (452).

In the present example, as shown in FIG. 12, a proximal portion of actuating member (470) protrudes proximally from handle portion (450). In some other versions, however, the proximal portion of actuating member (470) does not protrude proximally from handle portion (450).

FIG. 13 shows yet another exemplary tissue retrieval device (500). In this example, tissue retrieval device (500) comprises a handle portion (550), an introducer tube (520) extending distally from handle portion (550), a resilient hoop (580), and a retrieval bag (560). Introducer tube (520) is substantially identical to introducer tubes (20, 220) described above. Similarly, retrieval bag (560) is substantially identical to retrieval bags (60, 260) described above. Resilient hoop (580) is substantially identical to resilient arms (280) described above, except that resilient hoop (580) comprises just a single piece instead of two separate arms (280). Like resilient arms (280), resilient hoop (580) may be deployed relative to introducer tube (520) to a selected degree, to provide a selected degree of deployment and opening of retrieval bag (580).

Handle portion (550) of the present example comprises a fixed grip (552) and a clamshell trigger handle (554). Trigger handle (554) is pivotally coupled relative to fixed grip (552), such that trigger handle (554) is selectively pivotable toward fixed grip (552), about a pivot pin (556). Introducer tube (520) extends distally from handle portion (550). As described above, actuating rod (240) is translatable within introducer tube (520). An actuator (570) also couples trigger handle (554) with fixed grip (552) in the present example. In particular, a first end (572) of actuator (570) is coupled with trigger handle (554); while a second end (574) of actuator (570) is coupled with fixed grip (552). Actuator (570) is configured to advance an actuating rod (not shown) distally in introducer tube (520), to selectively advance and deploy resilient hoop (580) and retrieval bag (560), upon pivoting of trigger handle (554) about pivot pin (556) toward fixed grip (552). Such operation may result in full opening and deployment of retrieval bag (560) (e.g., similar to what is shown in FIG. 10, etc.) with just a single stroke of rotating trigger handle (554) about pivot pin (556) relative to fixed grip (552). Alternatively, tissue retrieval device (550) may require multiple strokes of rotating trigger handle (554) about pivot pin (556) relative to fixed grip (552) in order to achieve full opening and deployment of retrieval bag (560) (e.g., similar to what is shown in FIG. 10, etc.).

In some versions, the proximal end of the actuating rod in tissue retrieval device (500) includes a rack, as does second end (574) of actuator (570). These two racks may be coupled together via a pinion. Accordingly, as trigger handle (554) is rotated about pivot pin (556) toward fixed grip (552), this action drives actuator (570) into fixed grip (552); and as actuator (570) is so driven, the moving rack at second end (574) of actuator (570) rotates the pinion. This rotating pinion in turn drives the rack at the proximal end of the actuating rod distally, which causes resilient hoop (580) and retrieval bag (560) to deploy from the open distal end of introducer tube (520). Thus, this example operates very similar to tissue retrieval device (300) shown in FIG. 11 and described above, albeit with a slightly different mechanism to drive the rack at the proximal end of the actuating rod.

In some other versions, the proximal end of the actuating rod in tissue retrieval device (500) includes an actuating member with recesses, similar to actuating member (470) described above. First end (572) of actuator (570) is pivotally coupled with trigger handle (554); and second end (574) of actuator (570) provides a pawl that selectively engages recesses at the proximal end of the actuating rod. As trigger handle (554) is rotated about pivot pin (556) toward fixed grip (552), this action causes actuator (570) to rotate about its pivotal connection with trigger handle (554) at first end (572), which in turn drives second end (574) distally. This distal driving of second end (574) drives the actuating rod distally in an incremental fashion, thereby causing resilient hoop (580) and retrieval bag (560) to deploy from the open distal end of introducer tube (520) in an incremental fashion. Such an actuation stroke may be repeated as many times as needed in order to selectively deploy resilient hoop (580) and retrieval bag (560) to a desired degree. Thus, this example operates very similar to the exemplary tissue retrieval device shown in FIG. 12 and described above, albeit with a slightly different mechanism to drive the actuating member at the proximal end of the actuating rod.

Handle portion (550) of the present example also includes a locking member (558). Locking member (558) is configured to selectively lock the longitudinal position of the actuating rod relative to introducer tube (520). In some versions, locking member (558) is unlocked by default, and must be pressed in order to provide such a lock of the longitudinal position of actuating rod. For instance, locking member (558) may simply be pressed in once to provide such a lock, and may be released with such a lock being maintained (e.g., until locking member (558) is pressed again, etc.). Alternatively, locking member (558) may be configured such that the surgeon or other user must continue to press locking member (558) maintain such a lock. For instance, locking member (558) may include a spring or other component resiliently biasing locking member (558) to an unlocking position. As another merely illustrative variation, locking member (558) may be resiliently biased to maintain a locked position, such that a surgeon or other user must press and continue to press locking member (558) in order to allow the actuating rod to translate within introducer tube (520). In any such examples, locking member (558) may include a pawl or other feature that is selectively engaged relative to the actuating rod in order to selectively prevent or permit translation of the actuating rod relative to introducer tube (520). Various suitable ways in which locking member (558) may be provided and configured will be apparent to those of ordinary skill in the art in view of the teachings herein. It should also be understood that locking member (558) or some variation thereof may be incorporated into any other tissue retrieval device described herein. Of course, locking member (558) may simply be omitted if desired.

D. Exemplary Tissue Retrieval Device with Retrieval Bag Expansion

FIGS. 14-21 show the distal end and associated components of yet another exemplary tissue retrieval device. The tissue retrieval device of this example includes an introducer tube (620), a first actuating member (630), a second actuating member (650), and a tissue retrieval bag (670). Introducer tube (620) of the present example includes a recess (624) at its distal end. Recess (624) proximally terminates at a transverse wall (626) provided by introducer tube (620). The configuration of recess (624) gives distal opening (622) of introducer tube (620) a crescent shape, with introducer tube (620) having a cross-sectional profile defined by such a crescent shape along the length of recess (624). Of course, a crescent shape is merely optional, and any other suitable shapes may be used. The portion of introducer tube (620) proximal to transverse wall (626) is configured substantially identically to introducer tube (20) described above.

Figure 15:
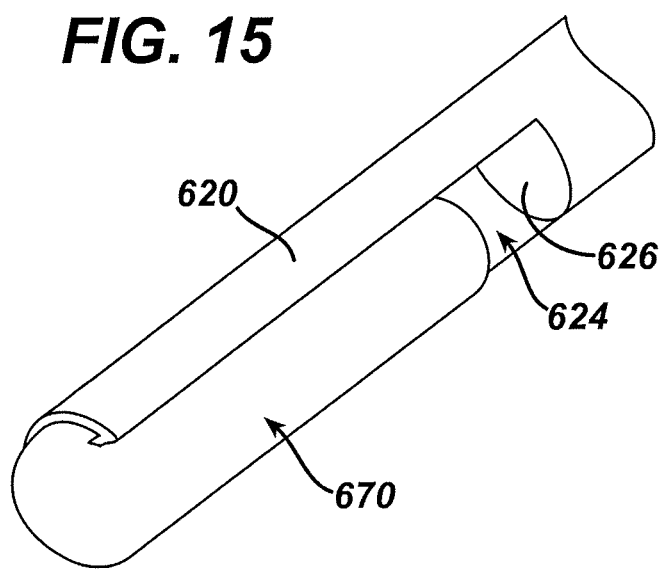
FIG. 15 is a perspective view of the distal end of the tissue retrieval device of FIG. 14, with a tissue retrieval bag in a stowed position.
Figure 16:
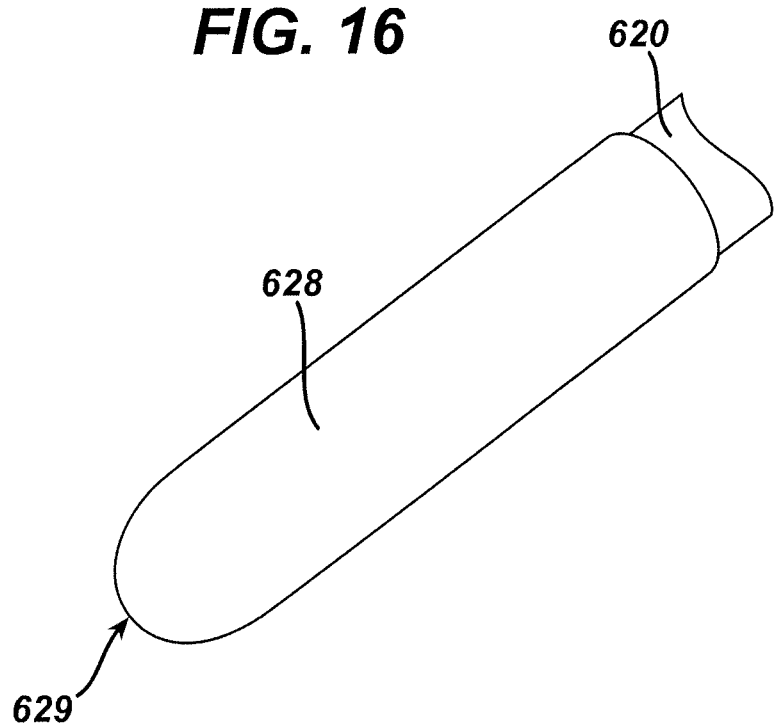
FIG. 16 is a perspective view of the distal end of the tissue retrieval device of FIG. 14, with a cap secured to the distal end of the tissue retrieval device.

As shown in FIG. 15, recess (624) is configured to accommodate a collapsed retrieval bag (670). In the present example, retrieval bag (670) is formed of a resilient material and is biased to shrink to a collapsed position. However, it should be understood that recess (624) may accommodate various other types of retrieval bags (670). As shown, retrieval bag (670) exits distal opening (622) of introducer tube (620) and is folded back proximally to fit in recess (624). In some versions, one or both actuating members (630, 650) are also folded back proximally to fit in recess (624) with retrieval bag (670). As shown in FIG. 16, a cap (628) is configured to slide over the distal end of introducer tube (620). In particular, cap (628) is configured to substantially contain retrieval bag (670) (and possibly also actuating members (630, 650), etc.) in recess (624).

Cap (628) of the present example has a closed and rounded distal end (629). Cap (628) may present an outer diameter that is between approximately 5 mm (inclusive) and approximately 15 mm (inclusive). Alternatively, cap (628) may have any other suitable dimension. In some versions, cap (628) has sufficient strength and/or rigidity to permit the distal end of introducer tube (620) to be used to perform blunt dissection of tissue. In addition or in the alternative, cap (628) may have some degree of flexibility. For instance, cap (628) may be configured to flex in a direction that is transverse to the longitudinal axis defined by introducer tube (620), such as at recess (624). In particular, in some uses it may be necessary to feed the distal end of introducer tube (620) through an insertion opening that provides a non-circular cross section and/or that presents an inner diameter that is less than approximately 5 mm. In some versions, the flexibility of cap (628), together with the flexibility of retrieval bag (670), may permit cap (628) and retrieval bag (670) to transversely collapse further into recess (624) to provide clearance through such a restricted insertion opening. In addition or in the alternative, at least part of retrieval bag (670) may change position within recess (624) during such deformation of cap (628) and/or retrieval bag (670) to provide clearance through such a restricted insertion opening. The surgeon or other user may rotate or rock introducer tube (620) about the longitudinal axis defined by introducer tube (620) when inserting the distal end of introducer tube (620) into such relatively difficult insertion openings, to facilitate such smashing and/or redistribution of retrieval bag (670) in recess (624).

Cap (628) may be removed from the distal end of introducer tube (620) in a variety of ways. For instance, a separate instrument (e.g., conventional tissue graspers, etc.) may be used to pull cap (628) distally off of introducer tube (620). Such a removed cap (628) may be placed in retrieval bag (670) after retrieval bag (670) has been deployed/opened. Alternatively, cap (628) may be disposed of in any other suitable fashion. As yet another merely illustrative alternative, cap (628) may be formed of an environmentally responsive material that causes cap (628) to break apart in the presence of an environmental condition associated with the interior of a patient (e.g., bodily fluids, carbon dioxide in an insufflated abdomen, temperature exceeding a threshold, etc.). For instance, cap (628) may be configured in accordance with the teachings of the degrading capsule described in U.S. patent application Ser. No. 12/693,491, entitled "Method of Fitting Pouch in Tissue Retrieval Device," filed Jan. 26, 2010, the disclosure of which is incorporated by reference herein. As yet another merely illustrative alternative, cap (628) may be substituted with a sheath that is retractable proximally relative to introducer tube (620), similar to sheath (108) described above. Still other suitable configurations, substitutes, supplements, and uses for cap (628) will be apparent to those of ordinary skill in the art in view of the teachings herein.

Figure 17:
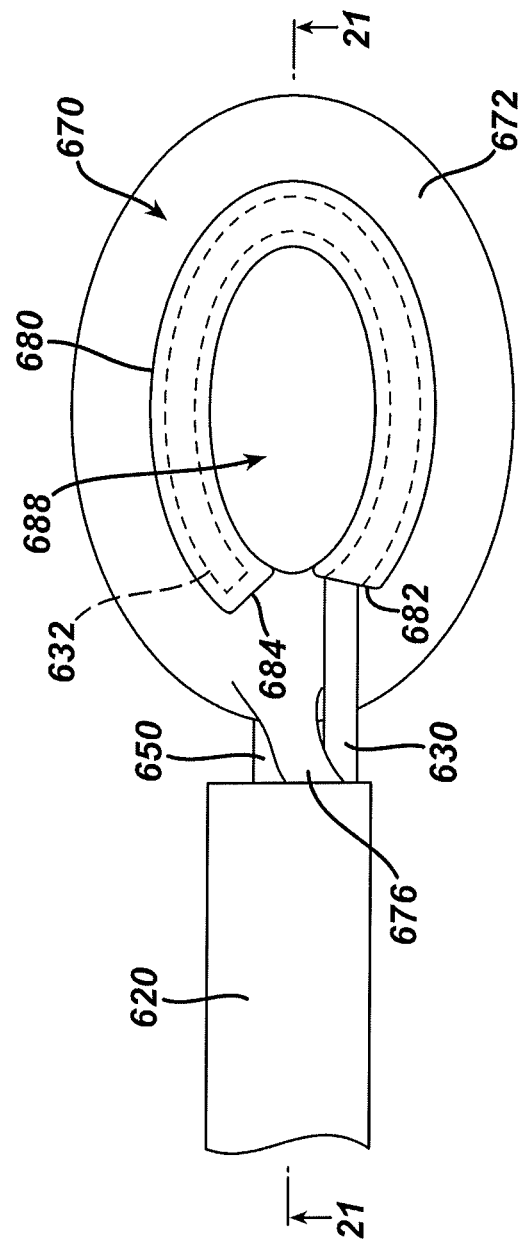
FIG. 17 is a top view of the distal end of the tissue retrieval device of FIG. 14, with the tissue retrieval bag in a deployed position.
Figure 18:
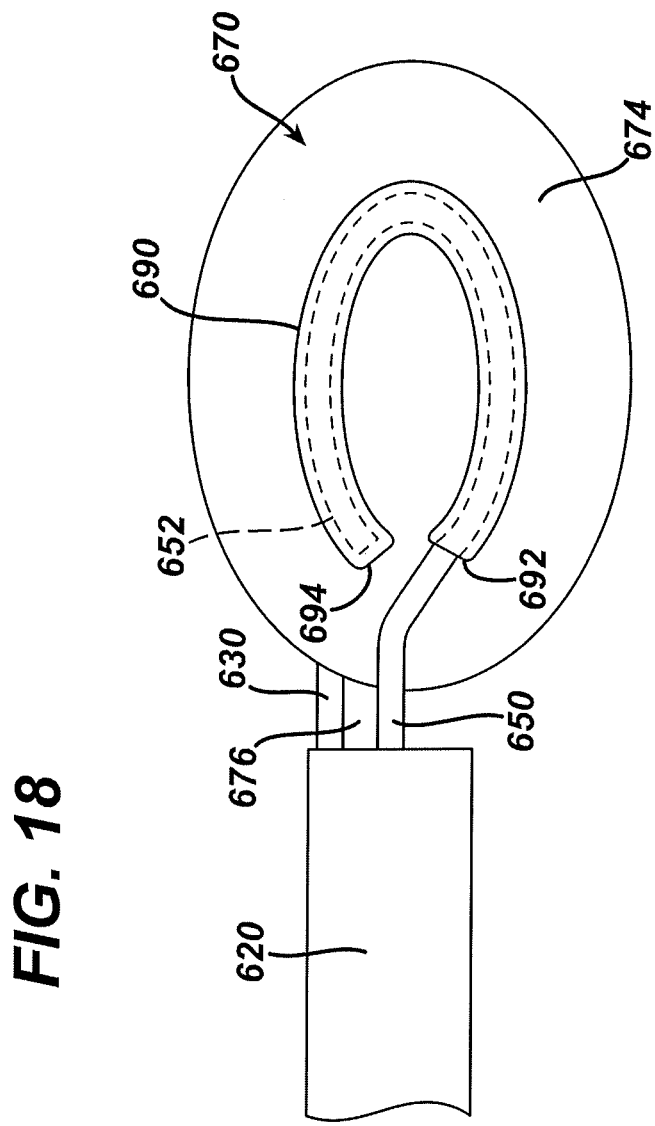
FIG. 18 is a bottom view of the distal end of the tissue retrieval device of FIG. 14, with the tissue retrieval bag in a deployed position.
Figure 19:
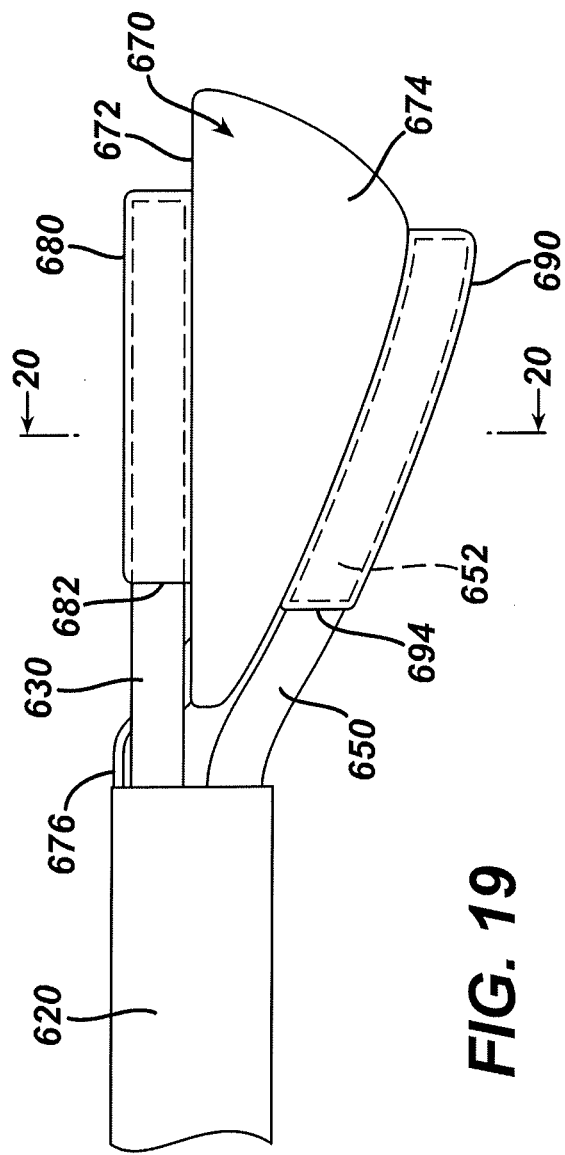
FIG. 19 is a side view of the distal end of the tissue retrieval device of FIG. 14, with the tissue retrieval bag in a deployed position.

As noted above, the tissue retrieval device of the present example comprises a first actuating member (630) and a second actuating member (650). Actuating members (630, 650) are translatable within introducer tube (620). First actuating member (630) terminates in a free end (632); and second actuating member (650) also terminates in a free end (652). Free ends (632, 652) may be retracted proximally relative to distal opening (622) (FIGS. 14-16) or may be extended distally relative to distal opening (622) (FIGS. 17-19). It should be understood that actuating members (630, 650) may be selectively translated relative to introducer tube (620) in a variety of ways. By way of example only, a thumb ring and finger grips may be used to translate actuating members (630, 650), in a manner similar to that described above with respect to thumb ring (42) and finger grips (24) being used to translate actuating rod (40). As another merely illustrative example, a pistol grip type of handle, similar to handle portions (350, 450) described above, may be used to translate actuating members (630, 650). As yet another merely illustrative example, a clamshell type of handle, similar to handle portion (550) described above, may be used to translate actuating members (630, 650). Alternatively, actuating members (630, 650) may be translationally driven in some other manual or mechanical fashion, electromechanically, pneumatically, hydraulically, or in any other suitable fashion. It should also be understood that a tissue retrieval device may be operable to translate actuating members (630, 650) substantially simultaneously or independently relative to each other.

Actuating members (630, 650) of the present example each comprise a deformable plastic beam. By way of example only, actuating members (630, 650) may be formed of low density polyethylene or polypropylene, etc. As can be seen in FIGS. 17-19, such beams are formed as vertically oriented strips that are configured to flex along a substantially horizontal plane yet that are also configured to resist flexing along a substantially vertical plane. Actuating members (630, 650) are thus rigid enough to support retrieval bag (670) when a tissue specimen (670) is placed in retrieval bag (670). As will be described in greater detail below, actuating members (630, 650) are configured to engage retrieval bag (670), and are further operable to stretch retrieval bag (670) from a contracted configuration to a stretched configuration. While actuating members (630, 650) are formed of plastic in the present example, it should be understood that actuating members (630, 650) may alternatively be formed of any other suitable material or combination of materials, including but not limited to metal, metal reinforced plastic, etc. Actuating members (630, 650) of the present example are resiliently biased to have a substantially straight configuration, but are easily deformable into curved configurations. Alternatively, actuating members (630, 650) may alternatively have any other suitable properties. In the present example, the configuration of the interior of introducer tube (620) keeps portions of actuating members (630, 650) that are disposed in introducer tube (620) in a substantially straight configuration, even as actuating members (630, 650) encounter longitudinal stresses. In particular, and as will be described in greater detail below, portions of actuating members (630, 650) that are exposed relative to introducer tube (620) are configured to curvingly buckle in response to compressive stresses; while portions of actuating members (630, 650) that are still disposed in introducer tube (620) stay substantially straight despite such compressive stresses.

Figure 20:
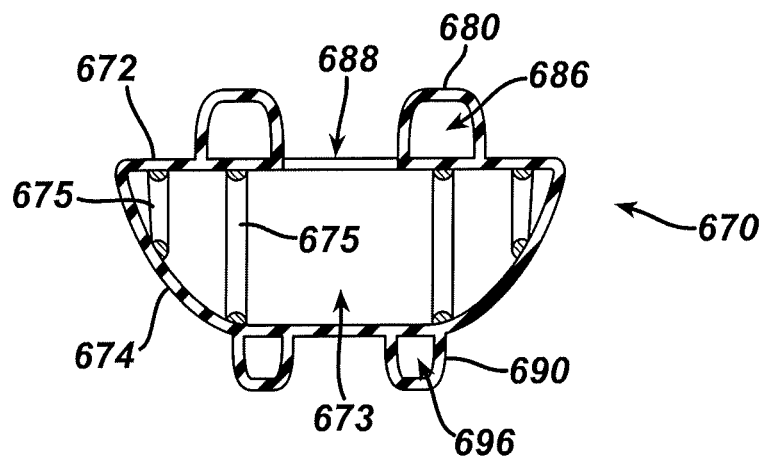
FIG. 20 is a cross-sectional view of the tissue retrieval bag of the tissue retrieval device of FIG. 14, taken along line 20-20 of FIG. 19, with a tail portion of the tissue retrieval bag omitted.
Figure 21:
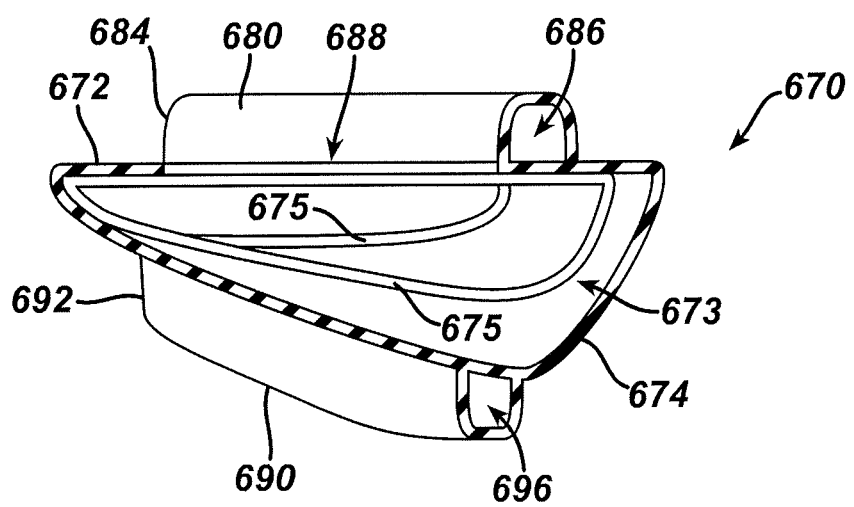
FIG. 21 is a cross-sectional view of the tissue retrieval bag of the tissue retrieval device of FIG. 14, taken along line 21-21 of FIG. 17, with a tail portion of the tissue retrieval bag omitted.

Retrieval bag (670) of the present example comprises a substantially flat top portion (672) and a rounded bowl-shaped bottom portion (674). A first extension (680) extends upwardly from top portion (672); while a second extension (690) extends downwardly from bottom portion (674). As best seen in FIGS. 20-21, first extension (680) defines a channel (686) that is configured to receive first actuating member (630). First extension (680) and channel (686) have a horseshoe shape in the present example, though it should be understood that first extension (680) and channel (686) may alternatively have any other suitable configuration. As seen in FIG. 17, channel (686) has an open end (682) that is configured to insertingly receive first actuating member (630); and a closed end (684) that is configured to arrest insertion of first actuating member (630) when free end (632) of first actuating member (630) engages closed end (684). As seen in FIGS. 19 and 21, first extension (680) and channel (686) extend along a substantially horizontal plane. Accordingly, and as shown in FIG. 19, first actuating member (630) stays substantially parallel to the longitudinal axis defined by introducer tube (620) when a distal portion of first actuating member (630) is fully disposed in channel (686). It should be understood that first extension (680) and/or channel (686) may alternatively have any other suitable orientation and/or configuration; and that first actuating member (630) may have any other suitable orientation when disposed in channel (686).

As can also be seen in FIGS. 20-21, second extension (690) defines a channel (696) that is configured to receive second actuating member (650). Second extension (690) and channel (696) have a horseshoe shape in the present example, though it should be understood that second extension (690) and channel (696) may alternatively have any other suitable configuration. As best seen in FIG. 18, channel (696) has an open end (692) that is configured to insertingly receive second actuating member (650); and a closed end (694) that is configured to arrest insertion of second actuating member (650) when free end (652) of second actuating member (650) engages closed end (694). The perimeter of second extension (690) is slightly smaller than the perimeter of first extension (680) in the present example, though it should be understood that extensions (680, 690) may alternatively have any other suitable sizing. As seen in FIGS. 19 and 21, second extension (690) and channel (696) extend along a plane that is oblique relative to the substantially horizontal plane along which first extension (680) and channel (686) extend. Accordingly, and as shown in FIG. 19, second actuating member (650) deflects downwardly relative to the longitudinal axis defined by introducer tube (620) when a distal portion of second actuating member (650) is fully disposed in channel (696). It should be understood that second extension (690) and/or channel (696) may alternatively have any other suitable orientation and/or configuration; and that second actuating member (650) may have any other suitable orientation when disposed in channel (696).

In the present example, when viewing the tissue retrieval device from the top and from the proximal end of the device toward the distal end of the device, open end (682) of top channel (686) is to the right of the longitudinal axis defined by introducer tube (620) while closed end (684) of top channel (686) is to the left of the longitudinal axis. By contrast, and also when viewing the tissue retrieval device from the top and from the proximal end of the device toward the distal end of the device, open end (692) of bottom channel (696) is to the left of the longitudinal axis defined by introducer tube (620) while closed end (694) of bottom channel (696) is to the right of the longitudinal axis.

Retrieval bag (670) further defines a top opening (688) adjacent to first extension (680). Top opening (688) is configured to permit tissue specimens to be placed within retrieval bag (688). In addition, retrieval bag (670) includes an integral tail portion (676) that is secured to the interior of introducer tube (620). While tail portion (676) is shown as entering open distal end (622) of introducer tube (620) at a vertical position that is above first actuating member (650), it should be understood that tail portion (676) may alternatively enter open distal end (622) at any other suitable vertical position. In some versions, the engagement of tail portion (676) with introducer tube (620) substantially grounds the proximal end of retrieval bag (670) to introducer tube (620) as retrieval bag (670) is stretched, as will be described in greater detail below. In some versions, tail portion (676) reinforced with a fabric, mesh, or some other structure(s), though this is not necessarily required in all versions. It should also be understood that tail portion (676) is merely optional.

Before retrieval bag (670) is to be deployed and opened in a patient, the tissue retrieval device of the present example may initially have a configuration similar to what is shown in FIG. 16. At this stage, retrieval bag (670) may be tucked within recess (624) under cap (629). Retrieval bag (670) may also have a resiliently contracted configuration. At this stage, free ends (632, 652) of actuating members (632, 652) may be at least partially disposed within their corresponding channels (686, 696) in retrieval bag (670). For instance, a first portion of retrieval bag (670) may remain within the hollow interior of introducer tube (620) to facilitate such a relationship, while a second portion of retrieval bag (670) is folded over to provide the configuration shown in FIG. 15. Alternatively, actuating members (632, 652) have any other suitable relationship with channels (686, 696) at this stage. The distal end of introducer tube (620) may then be inserted into the patient, via a trocar port, via an incision, or otherwise. Cap (629) may then be removed from the distal end of introducer tube (620) and may be dealt with in any suitable fashion. Retrieval bag (670) is thus exposed within the patient. At this stage, actuating members (630, 650) may be advanced distally. To the extent that free ends (632, 652) are not already in channels (686, 696), free ends (632, 652) may enter channels (686, 696) via corresponding open ends (682, 692). Various suitable ways in which free ends (632, 652) may be registered for insertion in channels (686, 696) upon distal advancement of actuating members (630, 650) will be apparent to those of ordinary skill in the art in view of the teachings herein.

As actuating members (630, 650) are advanced further distally, they each follow the horseshoe-like path provided by their respective channels (686, 696). The deformable properties of actuating members (630, 650), as well as the wall strength of extensions (680, 690) and the blunt configuration of free ends (632, 652), allow actuating members (630, 650) to follow the curved paths provided by channels (686, 696) without free ends (632, 652) poking through the walls of extensions (680, 690). In some versions, the walls of extensions (680, 690) are reinforced with a fabric, mesh, or some other structure(s), though this is not necessarily required in all versions. Engagement between tail portion (676) and introducer tube (620) keeps retrieval bag (670) grounded to introducer tube (620) during advancement of actuating members (630, 650) through channels (386, 396). Free ends (632, 652) eventually engage closed ends (684, 694) of channels (386, 396), resulting in a configuration as shown in FIGS. 17-19. At this stage, the distal portions of actuating members (630, 650) have deformed to provide curved configurations in accordance with the curvatures of channels (686, 696). In addition, the material forming retrieval bag (670) has slightly stretched to accommodate insertion of actuating members (630, 650). Alternatively, retrieval bag (670) may be configured such that retrieval bag (670) is still non-stressed or substantially non-stressed when free ends (632, 652) initially reach closed ends (684, 694) of channels (386, 396). At this stage, with free ends (632, 652) having initially reached closed ends (684, 694) of channels (386, 396), retrieval bag (670) still has a relatively small size and a relatively small internal volume (673), which can be accessed via top opening (688).

Retrieval bag (670) of the present example is formed of an elastomeric material and has a high degree of elasticity. By way of example only, retrieval bag (670) may be formed of polyisoprene. In addition or in the alternative, any other suitable material or combination of materials may be used. As noted above, retrieval bag (670) is resiliently biased to assume a substantially contracted configuration. However, the elasticity of retrieval bag (670) permits retrieval bag (670) to be expanded to significantly increase the capacity of the internal volume (673) defined by retrieval bag (670). Such expansion may be provided by continuing to advance actuating members (630, 650) distally, even after free ends (632, 652) have initially reached closed ends (684, 694) of channels (686, 696). With retrieval bag (670) being grounded to introducer tube (620) via tail portion (676), and with free ends (632, 652) being arrested by closed ends (684, 694), such continued distal advancement of actuating members (630, 650) will cause actuating members (630, 650) to buckle. Such buckling may cause the portions of actuating members (630, 650) that are disposed in channels (686, 696) to expand radially outwardly relative to the center of opening (688); other otherwise transversely outwardly relative to the longitudinal axis defined by introducer tube (620). Such outward buckling by actuating members (630, 650) may in turn stretch retrieval bag (670) outwardly. In addition, such continued distal advancement of first actuating member (630) may stretch top portion (672) of retrieval bag (670) distally in some versions; while continued distal advancement of second actuating member (630) may stretch bottom portion (674) of retrieval bag (670) distally and downwardly in some versions.

It should be understood that the stretching of retrieval bag (670) as described above may significantly increase the capacity of internal volume (673) defined by retrieval bag (670); as well as the size of top opening (688). By way of example only, retrieval bag (670) may be stretched such that its size increases by at least approximately 500% relative to its initial, non-stressed size. In addition, it should be understood that such stretching and expansion of retrieval bag (670) may increase the rigidity of actuating members (630, 650) and/or retrieval bag (670). In any event, with retrieval bag (670) stretched, a tissue specimen may be inserted into the increased internal volume (673) of retrieval bag (670) via top opening (688). It should also be understood that the stretched size of retrieval bag (670) may be selectively varied by the surgeon or other user, such as by selectively adjusting the extent to which actuating members (630, 650) are advanced distally. In other words, the surgeon or other user may advance actuating members (630, 650) distally until retrieval bag (670) has been stretched to a desired size. In some versions where retrieval bag (670) is formed of a material that is substantially resilient in addition to being stretchable, the resilient properties of retrieval bag (670) and/or any resiliency in actuating members (630, 650) themselves may produce backloading on actuating members (630, 650) when retrieval bag (670) has been actuated to a stretched configuration. In some such versions, the tissue retrieval device may include one or more components or features (e.g., a ratcheting mechanism, locking feature, etc.) that selectively maintains the longitudinal position of actuating members (630, 650) relative to introducer tube (620) when retrieval bag (670) has been actuated to a stretched configuration.

It should be understood that a stretchable tissue retrieval bag may include one or more features that are configured to influence the way in which the tissue retrieval bag stretches. For instance, such features may restrict stretching in a certain direction or dimension and/or promote stretching in a certain direction or dimension. Such features may also cause a stretchable tissue retrieval bag to stretch to a certain predetermined shape. In the present example, and as shown in FIGS. 20-21, retrieval bag (670) of the present example has a plurality of reinforcement members (675). In this example, reinforcement members (675) extend substantially longitudinally (i.e., parallel to a longitudinal axis defined by introducer tube (620)) and substantially vertically. Reinforcement members (675) are spaced apart from each other. Reinforcement members (675) are configured to substantially resist stretching. Accordingly, reinforcement members (675) of the present example substantially resist stretching of retrieval bag (670) in the longitudinal direction (i.e., parallel to a longitudinal axis defined by introducer tube (620)); while readily permitting stretching of retrieval bag outwardly (i.e., laterally transverse to a longitudinal axis defined by introducer tube (620)). Other suitable shapes and/or orientations for reinforcement members (675) (e.g., spiraled, asymmetric, etc.) will be apparent to those of ordinary skill in the art in view of the teachings herein.

Reinforcement members (675) of the present example comprise high tension strength composite fibers that are secured to the inner surfaces of the sidewalls of retrieval bag (670). Such fibers may have any suitable composition. Such fibers may also be provided within the sidewalls of retrieval bag (670), in addition to or in lieu of being secured to the inner surfaces of the sidewalls. As another merely illustrative example, reinforcement members (675) may comprise flexible metal, thermoformed plastic, fabric, aramid fibers such as Kevlar®, and/or any other suitable material or combination of materials. In some other versions, reinforcement members (675) comprise ribs formed by the sidewalls of retrieval bag (670). For instance, the material that forms the sidewalls of retrieval bag (670) may be bulked up in areas to define reinforcement members (675). Still other suitable ways in which reinforcement members (675) may be composed and configured will be apparent to those of ordinary skill in the art in view of the teachings herein.

In versions where retrieval bag (670) is formed of a material that is resilient in addition to being stretchable, the tension in retrieval bag (670) may be relieved by withdrawing actuating members (630, 650) proximally once a tissue specimen has been placed in a stretched retrieval bag (670). For instance, actuating members (630, 650) may be fully withdrawn such that they no longer pass through channels (686, 696); and such that actuating members (630, 650) are fully retracted within introducer tube (620). Even in versions where retrieval bag (670) is stretchable but substantially non-resilient, actuating members (630, 650) may still be withdrawn from channels (686, 696) to facilitate removal of retrieval bag (670) from the patient. It should be understood that, as actuating members (630, 650) are withdrawn proximally into introducer tube (620), the resilient properties of retrieval bag (670) may begin to shrink retrieval bag (670) back toward its non-stressed shape/configuration. Such shrinking of retrieval bag (670) about the tissue specimen may help secure the tissue specimen within retrieval bag (670) and at least partially close top opening (688) to substantially enclose the tissue specimen within retrieval bag (670). It should also be understood that retrieval bag (670) may include a closure string or other type of closing feature as described herein, particularly when the material forming retrieval bag (670) is stretchable yet substantially non-resilient. With retrieval bag (670) closed, retrieval bag (670) may be removed from the patient in any suitable fashion, including but not limited to those methods described herein.

In some versions where a closed retrieval bag (670) containing a tissue specimen is being pulled through an access opening (e.g., trocar port, incision in patient, etc.), such pulling may induce tensile stress in retrieval bag (670). In some such versions, the high elasticity of retrieval bag (670) may make such pulling relatively difficult, as retrieval bag (670) may have a tendency to simply stretch in response to such pulling instead of actually moving through the access opening (e.g., such as when the tissue specimen is significantly larger than the access opening, etc.). Thus, in some versions, particularly when such stretching of retrieval bag (670) is undesired, reinforcement members (675) may be configured to substantially resist such undesired stretching. For instance, retrieval bag (670) in the present example is configured to be removed from the patient by pulling retrieval bag (670) along a path that is substantially parallel to reinforcement members (675). Such a pulling orientation, as well as the substantially inelastic properties of reinforcement members (675), may substantially prevent undesired stretching of retrieval bag (670) as retrieval bag (670) is being removed from the patient along such a path.

It should also be understood that retrieval bag (670) may include one or more features that are configured to promote pulling of retrieval bag (670) in a removal direction that complements the configuration and/or orientation of reinforcement members (675) to avoid undesired stretching of retrieval bag (670). For instance, tail portion (676) may be severed from introducer tube (620) when the surgeon or other user is ready to remove retrieval bag (670) from the patient, and the surgeon or other user may remove retrieval bag (670) from the patient by extracorporeally pulling on tail portion (676). The position of tail portion (676) may promote such pulling in a direction that is substantially parallel to the orientation of reinforcement members (675), which may in turn substantially prevent undesired stretching of retrieval bag (670) as retrieval bag (670) is pulled from the patient by tail portion (676).

In some alternative versions, free ends (632, 652) are secured directly to introducer tube (620). In such versions, closed ends (684, 694) of channels (686, 696) are opened, such that actuating members (630, 650) pass completely through channels (686, 696). Other suitable features, components, configurations, and operabilities will be apparent to those of ordinary skill in the art in view of the teachings herein.

E. Other Exemplary Tissue Retrieval Devices

It should be understood that the components, features, and configurations of tissue retrieval devices shown in FIGS. 1-21 are merely exemplary. As one merely illustrative alternative, a tissue retrieval device, tissue retrieval bag, and/or related components/features may be configured in accordance with the teachings of U.S. patent application Ser. No. 12/692,670, entitled "Tissue Retrieval Device with Modular Pouch Cartridge," filed Jan. 25, 2010, the disclosure of which is incorporated by reference herein. As another merely illustrative example, a tissue retrieval device, tissue retrieval bag, and/or related components/features may be configured in accordance with the teachings of U.S. patent application Ser. No. 12/693,476, entitled "Tissue Retrieval Device with Pouch Stretching Arm," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,709, entitled "Tissue Retrieval Device with Buckling Arms," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,733, entitled "Tissue Retrieval Device with Bladders," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/692,727, entitled "Tissue Retrieval Device with Resilient Member," filed Jan. 25, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,485, entitled "Tissue Retrieval Device with Gusseted Pouch," filed Jan. 26, 2010, the disclosure of which is incorporated by reference herein. As yet another merely illustrative example, a tissue retrieval device, tissue retrieval bag, and/or related components/features may be configured in accordance with the teachings of U.S. patent application Ser. No. 12/693,491, entitled "Method of Fitting Pouch in Tissue Retrieval Device," filed Jan. 26, 2010, the disclosure of which is incorporated by reference herein. Furthermore, various ways in which the teachings herein may be combined with the teachings of any of the above-referenced patent applications will be apparent to those of ordinary skill in the art.

Still other suitable components, features, configurations, and operabilities that may be provided by a tissue retrieval device and/or tissue retrieval bag, etc. will be apparent to those of ordinary skill in the art in view of the teachings herein.

II. Exemplary Tissue Retrieval Bags

The following examples relate to various alternative ways in which a tissue retrieval bag may be configured. The below examples will be discussed mainly in the context of a tissue retrieval device (10) as shown in FIGS. 1-2 and described above. However, it should be understood that the below teachings of retrieval bag construction may be incorporated into virtually any other type of tissue retrieval device. By way of example only, any of the exemplary tissue retrieval bags described below may be readily incorporated into the context of a tissue retrieval device with a retractable sheath (108) as shown in FIGS. 5-6 and described above. Alternatively, any of the exemplary tissue retrieval bags described below may be readily incorporated into the context of the various tissue retrieval devices shown in FIGS. 7-19. Furthermore, the below teachings of various tissue retrieval bags may be readily incorporated into any of the tissue retrieval devices that are taught in the various patents and patent applications that are cited herein. Various suitable ways in which the below teachings tissue retrieval bags may be incorporated into such alternative tissue retrieval devices will be apparent to those of ordinary skill in the art in view of the teachings herein. Furthermore, other examples of tissue retrieval devices that may incorporate the below teachings of tissue retrieval bags will be apparent to those of ordinary skill in the art in view of the teachings herein.

Figure 22:
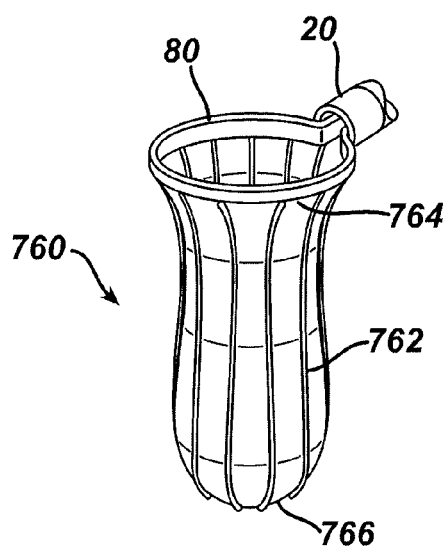
FIG. 22 is a perspective view of an exemplary alternative tissue retrieval bag.
Figure 23:
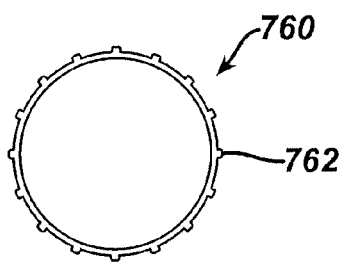
FIG. 23 is a top cross-sectional view of the tissue retrieval bag of FIG. 22.

FIGS. 22-23 show an exemplary alternative tissue retrieval bag (760) having vertically extending ribs (762). In particular, with retrieval bag (760) in a fully deployed and opened position as shown, ribs (762) extend along the length of retrieval bag (762), in a direction that is substantially perpendicular to the longitudinal axis defined by introducer tube (20). In this example, ribs (762) extend along the full length of retrieval bag (760)—from the open end (764) of retrieval bag (760) to the closed end (766) of retrieval bag (760). Alternatively, ribs (762) may extend along any other suitable length. In addition, while ribs (762) are spaced substantially equidistantly about the circumference of retrieval bag (760), it should be understood that ribs (762) may have any other suitable spacing or arrangement. As best seen in FIG. 23, ribs (762) of the present example extend radially outwardly from the sidewall of retrieval bag (760), though it should be understood that ribs (762) may alternatively extend radially inwardly from the sidewall of retrieval bag (760) or be positioned within the sidewall of retrieval bag (760).

Ribs (762) may have a configuration and serve a one or more functions similar to reinforcement members (675) described above. For instance, ribs (762) may comprise high tension strength composite fibers that are secured to the inner surfaces of the sidewall of retrieval bag (760). Such fibers may have any suitable composition. Such fibers may also be provided within the sidewall of retrieval bag (760), in addition to or in lieu of being secured to the inner surfaces of the sidewall. As another merely illustrative example, reinforcement ribs (762) may comprise flexible metal, thermoformed plastic, fabric, aramid fibers such as Kevlar®, and/or any other suitable material or combination of materials. In some other versions, ribs (762) are formed by the sidewall of retrieval bag (760). For instance, the material that forms the sidewall of retrieval bag (760) may be bulked up in areas to define ribs (762). Still other suitable ways in which ribs (762) may be composed and configured will be apparent to those of ordinary skill in the art in view of the teachings herein. It should also be understood that ribs (762) may substantially reinforce retrieval bag (760). For instance, the presence of ribs (762) may permit use of a material to form the sidewall of retrieval bag (760) that is substantially thinner than the material that might otherwise be used to form the sidewall of retrieval bag (760). In some versions where retrieval bag (760) is formed of a stretchable material, ribs (762) may also influence the way in which retrieval bag (760) stretches, similar to the influence described above in the context of reinforcement members (675) in retrieval bag (670). Of course, retrieval bag (760) may be formed of a non-stretchable material if desired, in which case ribs (762) may simply provide structural reinforcement to retrieval bag (760), particularly when a thin-walled version of retrieval bag (760) containing a tissue specimen is being pulled through a relatively tight access opening in a patient.

While retrieval bag (760) is shown as being mounted to a resilient hoop member (80) extending from an introducer tube (20) in accordance with the above teachings relating to tissue retrieval device (10), it should be understood that retrieval bag (760) may be readily incorporated into any other tissue retrieval device that is described herein or that is described in any patent or patent application that is referenced herein. Various ways in which retrieval bag (760) may be incorporated into such tissue retrieval devices will be apparent to those of ordinary skill in the art. Similarly, other various features, components, properties, configurations, and functionalities that may be incorporated into tissue retrieval bag (760) will be apparent to those of ordinary skill in the art in view of the teachings herein.

Figure 24:
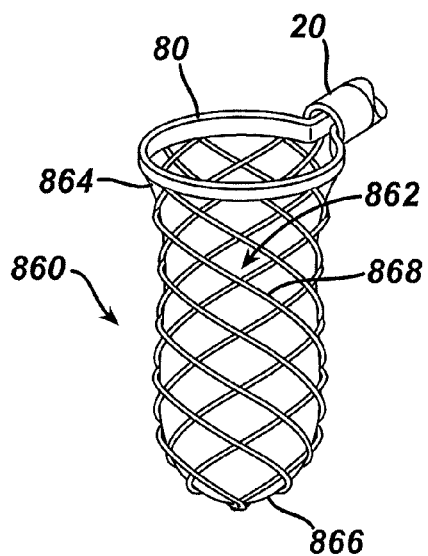
FIG. 24 is a perspective view of another exemplary alternative tissue retrieval bag.

FIG. 24 shows yet another exemplary alternative tissue retrieval bag (860). Retrieval bag (860) in this example includes a reinforcement mesh (862). Reinforcement mesh (862) is formed by a plurality of helically oriented reinforcement members (868) that intersect each other. While each reinforcement member (868) is helically oriented in the present example, it should be understood that one or more reinforcement members (868) may instead be oriented vertically, horizontally, or in any other suitable orientation, in addition to or in lieu of having reinforcement members (868) oriented helically. In this example, reinforcement members (868) extend along the full length of retrieval bag (860)—from the open end (864) of retrieval bag (860) to the closed end (866) of retrieval bag (860). Alternatively, reinforcement members (868) may extend along any other suitable length. It should also be understood that reinforcement members (868)

may extend outwardly from the sidewall of retrieval bag (860), extend inwardly from the sidewall of retrieval bag (860), and/or be positioned within the sidewall of retrieval bag (860).

Reinforcement members (868) may have a configuration and serve a one or more functions similar to reinforcement members (675) and ribs (762) described above. For instance, reinforcement members (868) may comprise high tension strength composite fibers that are secured to the inner surfaces of the sidewall of retrieval bag (860). Such fibers may have any suitable composition. Such fibers may also be provided within the sidewall of retrieval bag (860), in addition to or in lieu of being secured to the inner surfaces of the sidewall. As another merely illustrative example, reinforcement members (868) may comprise flexible metal, thermoformed plastic, fabric, aramid fibers such as Kevlar®, and/or any other suitable material or combination of materials. In some other versions, reinforcement members (868) are formed by the sidewall of retrieval bag (860). For instance, the material that forms the sidewall of retrieval bag (860) may be bulked up in areas to define reinforcement members (868). Still other suitable ways in which reinforcement members (868) may be composed and configured will be apparent to those of ordinary skill in the art in view of the teachings herein. It should also be understood that reinforcement members (868) may substantially reinforce retrieval bag (860). For instance, the presence of reinforcement members (868) may permit use of a material to form the sidewall of retrieval bag (860) that is substantially thinner than the material that might otherwise be used to form the sidewall of retrieval bag (860). In some versions where retrieval bag (860) is formed of a stretchable material, reinforcement members (868) may also influence the way in which retrieval bag (860) stretches, similar to the influence described above in the context of reinforcement members (675) in retrieval bag (670). Of course, retrieval bag (80) may be formed of a non-stretchable material if desired, in which case reinforcement members (868) may simply provide structural reinforcement to retrieval bag (860), particularly when a thin-walled version of retrieval bag (860) containing a tissue specimen is being pulled through a relatively tight access opening in a patient.

While retrieval bag (860) is shown as being mounted to a resilient hoop member (80) extending from an introducer tube (20) in accordance with the above teachings relating to tissue retrieval device (10), it should be understood that retrieval bag (860) may be readily incorporated into any other tissue retrieval device that is described herein or that is described in any patent or patent application that is referenced herein. Various ways in which retrieval bag (860) may be incorporated into such tissue retrieval devices will be apparent to those of ordinary skill in the art. Similarly, other various features, components, properties, configurations, and functionalities that may be incorporated into tissue retrieval bag (860) will be apparent to those of ordinary skill in the art in view of the teachings herein.

Figure 25:
FIG. 25 is a cross-sectional view showing the sidewall construction of another exemplary alternative tissue retrieval bag.
Figure 26:
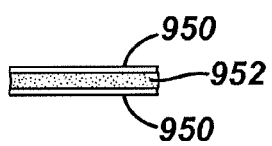
FIG. 26 is a cross-sectional view showing the sidewall construction of another exemplary alternative tissue retrieval bag.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethyelene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. FIGS. 25-26 show exemplary multilayer constructions that may be used to form the sidewall(s) of any tissue retrieval bag described herein. In particular, FIG. 25 shows a top layer (900) secured to a bottom layer (902) to form a sidewall of a retrieval bag. Top layer (900) is substantially thinner than bottom layer (902). In this example, a retrieval bag incorporating sidewall construction in accordance with FIG. 25 provides top layer (900) on the outside of the retrieval bag and bottom layer (902) on the inside of retrieval bag. Alternatively, this positioning may be reversed. Layers (900, 902) may comprise any of the materials listed above or any other suitable materials. FIG. 26 shows another merely exemplary multilayer construction, in which a middle layer (952) is sandwiched between to outer layers (950). Again, layers (950, 952) may comprise any of the materials listed above or any other suitable materials. Still other suitable multilayer constructions for forming retrieval bag sidewalls will be apparent to those of ordinary skill in the art in view of the teachings herein. It should also be understood that using more than one material to form retrieval bag sidewalls may allow relatively thinner layers to be used without compromising the structural integrity of the sidewalls.

Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

Figure 27:
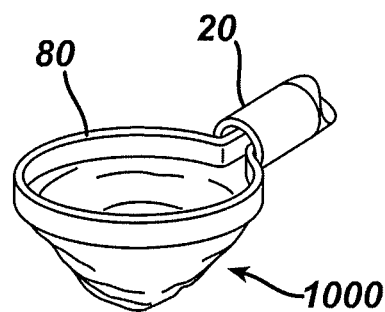
FIG. 27 is a perspective view of another exemplary alternative tissue retrieval bag, with the tissue retrieval bag in a contracted configuration.
Figure 28:
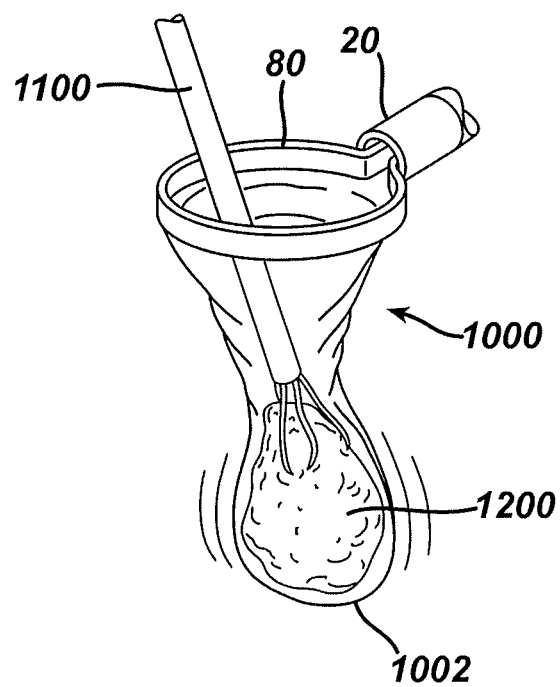
FIG. 28 is a perspective view of the tissue retrieval bag of FIG. 19, with a tissue specimen being inserted in the tissue retrieval bag to place the tissue retrieval bag in an expanded configuration.

As described above with reference to FIGS. 17-21, a tissue retrieval bag (670) may be formed of a stretchable material and may be stretched with components of the tissue retrieval device in order to receive and accommodate a tissue specimen. However, it should be understood that it may not be necessary to use one or more components of the tissue retrieval device in order to receive and accommodate a tissue specimen in a stretchable tissue retrieval bag. For instance, FIGS. 27-28 show an exemplary tissue retrieval bag (1000) that is formed of a stretchable material. In particular, FIG. 27 shows retrieval bag (1000) in a deployed but non-stressed state. FIG. 28 shows conventional tissue graspers (1100) being used to deposit a tissue specimen (1200) in retrieval bag (1000). In particular, tissue graspers (1100) are being used to exert a downward force on the closed bottom portion (1002) of retrieval bag (1000) via tissue specimen (1200), which in turn stretches the material of which retrieval bag (1000) is formed. Once tissue graspers (1100) release tissue specimen (1200) and are withdrawn from retrieval bag (1000), tissue specimen (1200) may remain in retrieval bag (1000) and may keep at least a portion of retrieval bag (1000) in a stretched state. However, while being elastic enough to stretch as shown, the material forming retrieval bag (1000) is not so resilient as to "spit out" tissue specimen (1200) by resiliently returning to the configuration shown in FIG. 27 as soon as tissue graspers (1100) release tissue specimen (1200) and are withdrawn from retrieval bag (1000).

Retrieval bag (1000) of FIGS. 27-28 may further include reinforcement members like reinforcement members (675) shown in FIGS. 20-21, ribs like ribs (762) shown in FIGS. 22-23, a mesh like mesh (862) shown in FIG. 24, or any other suitable features. In addition, while retrieval bag (1000) is shown as being mounted to a resilient hoop member (80) extending from an introducer tube (20) in accordance with the above teachings relating to tissue retrieval device (10), it should be understood that retrieval bag (1000) may be readily incorporated into any other tissue retrieval device that is described herein or that is described in any patent or patent application that is referenced herein. Various ways in which retrieval bag (1000) may be incorporated into such tissue retrieval devices will be apparent to those of ordinary skill in the art. Similarly, other various features, components, properties, configurations, and functionalities that may be incorporated into tissue retrieval bag (1000) will be apparent to those of ordinary skill in the art in view of the teachings herein.

It should also be understood that a stretchable tissue retrieval bag (670, 1000) may be resilient, partially resilient, or non-resilient. For instance, the material forming some versions of a stretchable tissue retrieval bag (670, 1000) is configured to stretched from a contracted configuration to a stretched configuration, and substantially maintain the stretched configuration without a significant resilient bias to return to the contracted configuration. In some such versions, the stretchable tissue retrieval bag (670, 1000) may be deployed in the contracted configuration and only be stretched enough to accommodate a tissue specimen. Such versions may eliminate a need to address back-loading that might otherwise occur from a bias of a resilient stretchable tissue retrieval bag (670, 1000). In some such versions, reinforcement members (675), a mesh (862), and/or some other type of feature may still restrict the degree to which the stretchable tissue retrieval bag (670, 1000); and may prevent or otherwise reduce undesirable further stretching of the stretchable tissue retrieval bag (670, 1000) as the filled stretchable tissue retrieval bag (670, 1000) is being pulled through a relatively tight access opening in a patient.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient.

In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted.

One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed.

Another merely exemplary additional feature that may be provided in any of the tissue retrieval instruments described herein includes retrieval bags having various sizes and geometries. For example, some tissue retrieval instruments may be designed with small, medium, or large retrieval bags. Also for example, some tissue retrieval instruments may use retrieval bags having pleats and/or gussets that allow for expansion when holding larger specimens.

It should also be understood that any of the tissue retrieval instruments and tissue retrieval bags described herein may be capable of receiving tissue specimens and removing tissue specimens from a patient without such tissue specimens needing to be morcellated or otherwise reduced in size before being received and removed by the tissue retrieval instrument and bag.

Still other suitable ways in which a tissue retrieval bag may be configured will be apparent to those of ordinary skill in the art in view of the teachings herein.

Regardless of which of the above described tissue retrieval bags and the above described tissue retrieval devices are being combined, it should be understood that the tissue retrieval bag may be packed or loaded in or relative to the tissue retrieval device in a variety of ways. By way of example only, the tissue retrieval bag may be packed or loaded in or relative to the tissue retrieval device in accordance with the teachings of U.S. patent application Ser. No. 12/693,491, entitled "Method of Fitting Pouch in Tissue Retrieval Device," filed Jan. 26, 2010, the disclosure of which is incorporated by reference herein. Various suitable ways in which the teachings of U.S. patent application Ser. No. 12/693,491 may be incorporated into the teachings herein will be apparent to those of ordinary skill in the art. Similarly, various other suitable ways in which a tissue retrieval bag as described herein may be packed or loaded in or relative to a tissue retrieval device as described herein will be apparent to those of ordinary skill in the art in view of the teachings herein.

III. Other

While several retrieval bags, deployment mechanisms, and other features of tissue retrieval devices have been discussed in detail above, it should be understood that the components, features, configurations, and methods of using the bags, deployment mechanisms, and other features are not limited to the contexts provided above. For instance, components, features, configurations, and methods of use described in the context of one of the tissue retrieval devices may be incorporated into any of the other retrieval devices. Similarly, components, features, configurations, and methods of use described in the context of one of the retrieval bags may be incorporated into any of the other retrieval bags. Various suitable ways in which the teachings herein may be combined and interchanged will be apparent to those of ordinary skill in the art. In addition, other suitable alternative components, features, configurations, and methods of using the above-described retrieval devices will be apparent to those of ordinary skill in the art in view of the teachings herein.

While the tissue retrieval instruments of the above-described examples are actuated manually by advancing a thumb ring distally relative to finger rings, by manually retracting a sheath, by squeezing a pistol grip, by squeezing a clamshell grip, or in some other manual fashion, it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

As noted above, the various versions of tissue retrieval devices described herein, including but not limited to the various versions of retrieval bags described herein, may be used in a conventional endoscopic procedure that includes the insertion of the introducer tube or other component through a small opening, e.g., an incision, natural orifice, or trocar access port, etc. Of course, tissue retrieval devices may be used in conjunction with any other suitable surgical or medical procedure, such as endoscopic/laparoscopic procedures, open surgical procedures, or robotic-assisted surgery, etc. Still other various settings and combinations in which a tissue retrieval device or tissue retrieval bags may be used will be apparent to those of ordinary skill in the art in view of the teachings herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:
1. A specimen retrieval instrument, comprising:
(a) a tubular member having a distal end;
(b) one or more frame members, wherein the one or more frame members are movable relative to the tubular member, and wherein the one or more frame members are resiliently biased to together define an hourglass configuration comprising a distal convex portion, and a proximal convex portion, and a concave portion defined between the distal convex portion and the proximal convex portion, wherein each portion is configured to cooperate with the distal end of the tubular member, and wherein the distal convex portion and the proximal convex portion are each configured to abut the wall defining the opening of the distal end when advanced through the tubular member to extend at least a portion of the one or more frame members distally relative to the tubular member; and
(c) a retrieval bag, wherein the retrieval bag is secured to the one or more frame members, wherein the retrieval bag is movable from a non-deployed position to a first deployed position, wherein the retrieval bag is further movable from the first deployed position to a second deployed position, wherein the retrieval bag provides a first internal capacity when the retrieval bag is in the first deployed position, wherein the retrieval bag provides a second internal capacity when the retrieval bag is in the second deployed position, wherein the second internal capacity is greater than the first internal capacity;
wherein the retrieval bag is configured to be closed and removed from the one or more frame members in the first deployed position, and wherein the retrieval bag is configured to be closed and removed from the one or more frame members in the second deployed position.

2. The specimen retrieval instrument of claim 1, wherein the one or more frame members comprise a pair of resilient arms.

3. The specimen retrieval instrument of claim 2, wherein the resilient arms are resiliently biased together to define an hourglass configuration, wherein a distal end of one resilient arm is spaced from a distal end of the other resilient arm.

4. The specimen retrieval instrument of claim 1, wherein the retrieval bag is entirely disposed within the tubular member when the retrieval bag is in the non-deployed position.

5. The specimen retrieval instrument of claim 4, wherein a first part of the retrieval bag remains disposed in the tubular member when the retrieval bag is in the first deployed position, wherein a second part of the retrieval bag is exposed relative to the tubular member when the retrieval bag is in the first deployed position, wherein the second part of the retrieval bag provides the first internal capacity.

6. The specimen retrieval instrument of claim 5, wherein the first and second parts of the retrieval bag are exposed relative to the tubular member when the retrieval bag is in the second deployed position, wherein the first and second parts of the retrieval bag together provide the second internal capacity.

7. The specimen retrieval instrument of claim 1, wherein the retrieval bag is formed of a stretchable material, wherein the retrieval bag is stretchable from the first deployed position to the second deployed position to increase the first internal capacity to the second internal capacity.

8. The specimen retrieval instrument of claim 7, wherein the retrieval bag is resiliently biased to assume a contracted configuration, wherein the retrieval bag is in the contracted configuration when the retrieval bag is in the non-deployed position.

9. The specimen retrieval instrument of claim 7, wherein the retrieval bag defines one or more channels configured to receive the one or more frame members, wherein the one or more frame members are movable to stretch the retrieval bag from the first deployed position to the second deployed position.

10. The specimen retrieval instrument of claim 1, wherein the retrieval bag further comprises at least one sidewall having one or more reinforcement members, wherein the one or more reinforcement members are configured to structurally reinforce the at least one sidewall.

11. The specimen retrieval instrument of claim 10, wherein the reinforcement members are selected from the group consisting of ribs, fibers, and a mesh.

12. The specimen retrieval instrument of claim 10, wherein the retrieval bag is formed of a stretchable material, wherein the one or more reinforcement members are configured to restrict stretching of the at least one sidewall in one or more directions.

13. The specimen retrieval instrument of claim 1, further comprising a handle portion, wherein the handle portion includes a trigger member in communication with the one or more frame members, wherein the trigger member is operable to transition the retrieval bag from the non-deployed position to the first deployed position in response to at least one stroke of the trigger member, wherein the trigger member is further operable to transition the retrieval bag from the first deployed position to the second deployed position in response to at least one additional stroke of the trigger member.

14. A specimen retrieval instrument, comprising:
(a) a tubular member having a distal end, wherein the distal end includes an opening, wherein a wall defines the opening of the distal end;
(b) a pair of resilient arms, wherein the pair of resilient arms are movable relative to the tubular member to extend at least a portion of the pair of resilient arms distally relative to the tubular member, and wherein the pair of resilient arms are resiliently biased to together define an hourglass configuration comprising a distal convex portion, a proximal convex portion, and a concave portion defined between the distal convex portion and the proximal convex portion, wherein each portion is configured to cooperate with the distal end of the tubular member, and wherein the distal convex portion and the proximal convex portion are each configured to abut the wall defining the opening of the distal end when advanced through the tubular member; and
(c) a retrieval bag, wherein the retrieval bag is secured to the pair of resilient arms, wherein the retrieval bag is movable from a non-deployed position to a first deployed position, wherein the retrieval bag is further movable from the first deployed position to a second deployed position, wherein the retrieval bag provides a first internal capacity when the retrieval bag is in the first deployed position, wherein the retrieval bag provides a second internal capacity when the retrieval bag is in the second deployed position, wherein the second internal capacity is greater than the first internal capacity, wherein the retrieval bag is configured to be closed and removed from the pair of resilient arms in the first deployed position, and wherein the retrieval bag is configured to be closed and removed from the pair of resilient arms in the second deployed position.

\* \* \* \* \*